(12) United States Patent
Henao et al.

(10) Patent No.: US 9,394,214 B2
(45) Date of Patent: Jul. 19, 2016

(54) OXYGEN STORAGE AND PRODUCTION OF $C_{5+}$ HYDROCARBONS

(71) Applicant: ExxonMobil Chemical Patents Inc., Baytown, TX (US)

(72) Inventors: Juan D. Henao, Houston, TX (US); Paul F. Keusenkothen, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 161 days.

(21) Appl. No.: 14/469,141

(22) Filed: Aug. 26, 2014

(65) Prior Publication Data

US 2015/0065769 A1 Mar. 5, 2015

Related U.S. Application Data

(60) Provisional application No. 61/872,175, filed on Aug. 30, 2013.

(51) Int. Cl.
*C07C 5/327* (2006.01)
*C07C 5/333* (2006.01)
(Continued)

(52) U.S. Cl.
CPC ............ *C07C 2/84* (2013.01); *B01J 8/0207* (2013.01); *B01J 15/005* (2013.01); *B01J 19/24* (2013.01); *B01J 19/245* (2013.01); *C07C 2/08* (2013.01); *C07C 2/42* (2013.01); *C07C 2/78* (2013.01); *C07C 5/48* (2013.01); *C07C 7/005* (2013.01);
(Continued)

(58) Field of Classification Search
CPC ............ C07C 5/327; C07C 5/333; C07C 2/42
USPC .......................... 585/319, 324, 943, 658, 407
See application file for complete search history.

(56) References Cited

U.S. PATENT DOCUMENTS 3,435,089 A  3/1969  Moore, Jr. et al.
4,144,277 A  3/1979  Walker et al.
(Continued)

FOREIGN PATENT DOCUMENTS

DE  275 452  1/1990
FR  1 588 738  4/1970
(Continued)

OTHER PUBLICATIONS

Aguado et al., "*Absolute Molecular Sieve Separation of Ethylene/Ethane Mixtures with Silver Zeolite A*," Journal of the American Chemical Society 2012, vol. 134, pp. 14635-14637.
Ghose et al., "Solution Combustion Synthesized Catalytic Materials for Oxidative Coupling of Methane," 23rd North American Catalysis Society Meeting, Jun. 5, 2013. (Extended Abstract).
(Continued)

*Primary Examiner* — Thuan D Dang

(57) ABSTRACT

Disclosed are reactors and reaction processes for contacting hydrocarbon reactant in the presence of oxygen stored and released within a thermal mass region of the reactor, and catalytically converting at least a portion of alkane, e.g., methane, in the hydrocarbon reactant to produce a reaction mixture comprising a $C_{5+}$ composition. Oxygen storage and release for carrying out the catalytic conversion is achieved by including an oxygen storage material in a thermal mass region of the reactor. Flow-through reactors can be used to carry out oxygen storage and the hydrocarbon conversion reactions. Reverse-flow reactors are examples of flow-through reactors, which can be used to carry out oxygen storage and the hydrocarbon conversion reactions.

14 Claims, 1 Drawing Sheet

(51) Int. Cl.

| | | |
|---|---|---|
| *C07C 2/42* | (2006.01) | |
| *C07C 2/84* | (2006.01) | |
| *C07C 7/12* | (2006.01) | |
| *B01J 8/02* | (2006.01) | |
| *B01J 19/24* | (2006.01) | |
| *C07C 2/08* | (2006.01) | |
| *C07C 5/48* | (2006.01) | |
| *C07C 7/00* | (2006.01) | |
| *B01J 15/00* | (2006.01) | |
| *C07C 2/78* | (2006.01) | |
| *B01D 53/04* | (2006.01) | |

(52) U.S. Cl.
CPC . *C07C 7/12* (2013.01); *B01D 53/04* (2013.01); *B01D 2256/24* (2013.01); *B01D 2257/7022* (2013.01); *B01D 2259/4009* (2013.01); *B01J 2208/0053* (2013.01); *B01J 2208/00309* (2013.01); *B01J 2208/00548* (2013.01); *B01J 2208/00557* (2013.01); *B01J 2208/00566* (2013.01); *B01J 2219/24* (2013.01); *B01J 2219/2402* (2013.01); *Y02P 20/51* (2015.11)

(56) References Cited

U.S. PATENT DOCUMENTS

| 4,751,336 | A | | 6/1988 | Jezl et al. |
|---|---|---|---|---|
| 4,754,093 | A | | 6/1988 | Jezl et al. |
| 4,754,095 | A | | 6/1988 | Coughenour et al. |
| 4,988,660 | A | * | 1/1991 | Campbell ............. B01J 23/002 502/302 |
| 5,095,161 | A | | 3/1992 | Abrevaya et al. |
| 5,336,825 | A | | 8/1994 | Choudhary et al. |
| 5,936,135 | A | | 8/1999 | Choudhary et al. |
| 6,258,993 | B1 | | 7/2001 | Carr et al. |
| 7,022,888 | B2 | | 4/2006 | Choudhary et al. |
| 2002/0020113 | A1 | | 2/2002 | Kennedy et al. |
| 2009/0292153 | A1 | | 11/2009 | Cai et al. |
| 2010/0290978 | A1 | | 11/2010 | Chun et al. |
| 2011/0315012 | A1 | | 12/2011 | Kuznicki et al. |
| 2011/0320176 | A1 | | 12/2011 | Haldoupis et al. |
| 2014/0018589 | A1 | | 1/2014 | Iyer et al. |
| 2015/0065767 | A1 | | 3/2015 | Henao et al. |
| 2015/0065771 | A1 | | 3/2015 | Keusenkothen |
| 2015/0065773 | A1 | | 3/2015 | Henao et al. |

FOREIGN PATENT DOCUMENTS

| GB | 855 764 | 12/1960 |
|---|---|---|
| WO | WO 91/04240 | 4/1991 |
| WO | WO 95/20556 | 8/1995 |
| WO | WO 02/24614 | 3/2002 |
| WO | WO 2007/075945 | 7/2007 |
| WO | WO 2011/149996 | 12/2011 |

OTHER PUBLICATIONS

Jiang et al., "Methane to Ethylene with 85 Percent Yield in a Gas Recycle Electrocatalytic Reactor-Separator", Science, vol. 264, No. 5165, Jun. 10, 1994, pp. 1563-1566.
Keller et al., "Synthesis of Ethylene via Oxidative Coupling of Methane", Journal of Catalysis 73 (1982), pp. 9-19.
Korf et al., "The Development of Doped Li/MgO Catalyst Systems for the Low-Temperature Oxidative Coupling of Methane", Methane Conversion by Oxidative Processes—Fundamental and Engineering Aspects, Van Nostrand Reinhold / Springer, US, pp. 168-199, 1992.
Kruglov et al. "Optimization of the Simulated Countercurrent Moving-Bed Chromatographic Reactor for the Oxidative Coupling of Methane," Chemical Engineering Science, vol. 51, No. 11 (1996), pp. 2945-2950.
Liu et al., "Autothermal Reforming of Methane in a Reverse-Flow Reactor", Chemical Engineering & Technology, vol. 32, No. 9, Sep. 1, 2009, pp. 1358-1366.
Machocki et al., "Methane Oxidative Coupling in an Undiluted Reactor Mixture in a Reactor-Adsorber System With Gas Recirculation," Applied Catalysis A: General 146 (1996), pp. 391-400.
Mattisson, T., *"Materials for Chemical-Looping with Oxygen Uncoupling,"* Hindawi Publishing Corporation, ISRN Chemical Engineering, vol. 2013, Article ID 526375, 19 pages.
Mehdipour et al., "Modeling of a PSA-TSA Process for Separation of CH4 from C2 Products of OcM Reaction," Separation Science and Technology, vol. 47, No. 8 (2012), pp. 1199-1212.
Mleczko et al., "Catalytic Oxidative Coupling of Methane—Reaction Engineering Aspects and Process Schemes," Fuel Processing Technology, Elsevier BV, NL, vol. 42, No. 2-3, Apr. 1, 1995, pp. 217-248.
Mortazavi et al., "Catalytic Methane Coupling Under Periodic Operation", The Canadian Journal of Chemical Engineering, vol. 74, No. 5, Oct. 1, 1996, pp. 683-694.
Olivier et al., "High-Temperature Parallel Screening of Catalysts for the Oxidative Coupling," Catalysis Today, vol. 137 (2008), pp. 80-89.
SRI, Ethylene from Methane, Process Economics Program Report No. 208 (Jan. 1994), 139 pages.
Tonkovich et al., "Enhanced C2 Yields from Methane Oxidative Coupling by Means of a Separative Chemical Reactor", Science, vol. 262, No. 5131, Oct. 8, 1993, pp. 221-223.
Veser et al., "Multiscale Process Intensification for Catalytic Partial Oxidation of Methane: From Nanostructured Catalysts to Integrated Reactor Concepts", Catalysis Today, Elsevier, NL, vol. 157, No. 1-4, Nov. 17, 2010, pp. 24-32.
Yentekakis et al., "Oxidative Coupling of Methane to Ethylene with 85% Yield in a Gas Recycle Electrocatalytic Reactor Separator," Studies in Surface Science and Catalysis, vol. 107 (1997), pp. 307-312.
Bloch et al., *"Hydrocarbon Separations in a Metal Organic Framework with Open Iron(II) Coordination Sites,"* Science, vol. 335, pp. 1606-1610, 2012.
Centi et al., *"Direct Conversion of Methane, Ethane and Carbon Dioxide to Fuels and Chemicals,"* The Catalyst Group Resources Inc., Spring House, 2008, 222 pages.
Choudhary et al., *"Low-Temperature Nonoxidative Activation of Methane over H-Galloaluminosilicate (MFI) Zeolite,"* Science, vol. 275, pp. 1286-1288, 1997.
Choudhary et al., *"Product Selectivity and Aromatics Distribution in Aromatization of Propane Over H—GaMFI Zeolite: Influence of Temperature,"* Microporous and Mesoporous Materials, vol. 23, Issues 3-4, pp. 231-238, 1998.
Das et al., *"Interplay of Metalloligand and Organic Ligand to Tune Micropores within Isostructural Mixed-Metal Organic Frameworks (M'MOFs) for Their Highly Selective Separation of Chiral and Achiral Small Molecules,"* Journal of the American Chemical Society, vol. 134, Issue 20, pp. 8703-8710, 2012.
Gucuyener et al., *"Ethane/Ethene Separation Turned on Its Head: Selective Ethane Adsorption on the Metal-Organic Framework ZIF-7 through a Gate-Opening Mechanism,"* Journal of the American Chemical Society, vol. 132, Issue 50, pp. 17704-17706, 2010.
Guo et al., *"Dehydrogenation and Aromatization of Propane over Rhenium-Modified HZSM-5 Catalyst,"* Journal of Molecular Catalysis A: Chemical, vol. 239, Issue 1-2, pp. 222-227, 2005.
Guo et al., *"Energy Efficient Coaromatization of Methane and Propane,"* Journal of Natural Gas Chemistry, vol. 18, Issue 3, pp. 260-272, 2009.
He et al., *"High Separation Capacity and Selectivity of $C_2$ Hydrocarbons over Methane with a Microporous Metal-Organic Framework at Room Temperature,"* Chemistry—A European Journal, vol. 18, Issue 7, pp. 1901-1904, 2012.
Liu et al., *"Scale Up and Stability Test for Oxidative Coupling of Methane Over $Na_2WO_4$—$Mn/SiO_2$ Catalyst in a 200 ml Fixed-Bed Reactor,"* Journal of Natural Gas Chemistry, vol. 17, No. 1, pp. 59-63, Mar. 2008.
Tonkovich et al., *"A Simulated Countercurrent Moving-Bed Chromatographic Reactor for the Oxidative Coupling of Methane: Experimental Results,"* Chemical Engineering Science, vol. 49, No. 24, pp. 4647-4656, 1994.

* cited by examiner

OXYGEN STORAGE AND PRODUCTION OF C$_{5+}$ HYDROCARBONS

CROSS-REFERENCE TO RELATED APPLICATION(S)

This application claims priority to and the benefit of (i) U.S. Provisional Patent Application No. 61/872,175, filed Aug. 30, 2013; (ii) E.P. Patent Application No. 13189746.4, filed Oct. 22, 2013; and (iii) U.S. Provisional Patent Application No. 61/912,901, filed Dec. 6, 2013; the contents of which are incorporated herein by reference in their entireties. The following related cases are also incorporated by reference in their entireties: (i) P.C.T. Patent Application No. PCT/US2014/052698, filed Aug. 26, 2014; (ii) U.S. patent application Ser. No. 14/469,109, filed Aug. 26, 2014; (iii) P.C.T. Patent Application No. PCT/US2014/052715, filed Aug. 26, 2014; (iv) U.S. patent application Ser. No. 14/469,180, filed Aug. 26, 2014; (v) P.C.T. Patent Application No. PCT/US2014/052722, filed Aug. 26, 2014; (vi) U.S. patent application Ser. No. 14/469,227, filed Aug. 26, 2014; and (vii) P.C.T. Patent Application No. PCT/US2014/052710, filed Aug. 26, 2014.

FIELD OF THE INVENTION

The invention relates to processes for catalytically converting alkane to higher molecular weight compositions. The invention further relates to processes for oxygen storage and catalytically converting methane-containing feeds to produce C$_{5+}$ hydrocarbon compositions, and to equipment useful in such processes.

BACKGROUND OF THE INVENTION

Although methane is abundant, its relative inertness has limited its utility in conversion processes for producing higher-value hydrocarbon. For example, oxidative coupling methods generally involve highly exothermic and potentially hazardous methane combustion reactions, which frequently require expensive oxygen generation facilities, and produce large quantities of environmentally sensitive carbon oxides. In order to overcome some of these difficulties, there has been considerable effort directed toward methane conversion via catalytic oxidative coupling reactions.

One process for producing ethylene from methane by catalytic oxidative coupling is disclosed in *Synthesis of Ethylene via Oxidative Coupling of Methane*, G. E. Keller and M. H. Bhasin, Journal of Catalysis 73, 9-19 (1982). Although an appreciable selectivity to ethylene was observed (to a maximum of about 50%), conversion was relatively low. In order to overcome the methane-ethylene separation difficulties resulting from the low methane conversion, technology has been developed for quenching the reaction product downstream of the oxidative coupling reactor, and then separating ethylene from the unreacted methane.

One process, disclosed in *Enhanced C$_2$ Yields from Methane Oxidative Coupling by Means of a Separative Chemical Reactor*, A. E. Tonkovich, R. W. Carr, R. Aris, Science 262, 221-223, 1993, includes a simulated countercurrent moving-bed chromatographic reactor, and achieves 65% methane conversion and 80% selectivity to C$_2$ hydrocarbons. The reactor is configured in four sections, with each section comprising (i) a catalytic reactor containing Sm$_2$O$_3$ catalyst and (ii) an adsorbent column located downstream of the catalytic reactor. Methane and oxygen react via catalytic oxidative coupling in the reactor at a temperature in the range of about 900° K to 1100° K, and then ethylene is separated from unreacted methane in the sorption column. In order to maintain sufficient selectivity for ethylene sorption, the reactor's product is quenched to a temperature of 373° K in the sorption column. In another process, disclosed in *Methane to Ethylene with 85 Percent Yield in a Gas Recycle Electrocatalytic Reactor-Separator*, Y. Jiang, I. V. Yentekakis, C. G. Vayenas, Science 264, 1563-1566, 1994, gas recycle is utilized to further increase methane conversion, but an even lower quench temperature (30° C.) is used during ethylene sorption.

Catalytic processes have also been proposed for co-converting methane and one or more co-reactants to higher hydrocarbon, such as aromatics. For example, U.S. Pat. No. 5,936,135 discloses reacting methane at a temperature in the range of 300° C. to 600° C. with (i) a C$_{2-10}$ olefin and/or (ii) a C$_{2-10}$ paraffin in the presence of a bifunctional pentasil zeolite catalyst, having strong dehydrogenation and acid sites, to produce aromatics. The preferred mole ratio of olefin and/or higher paraffin to methane and/or ethane in the feed ranges from about 0.2 to about 2.0.

Other processes utilize organic oxygenate as a co-reactant for the non-oxidative methane conversion to produce higher hydrocarbon, including aromatics. For example, U.S. Pat. No. 7,022,888 discloses a process for the non-oxidative conversion of methane simultaneously with the conversion of an organic oxygenate, represented by a general formula: C$_n$H$_{2n+1}$OC$_m$H$_{2m+1}$, wherein C, H and O are carbon, hydrogen and oxygen, respectively; n is an integer having a value between 1 and 4; and m is an integer having a value between zero and 4. The methane and oxygenate are converted to C$_{2+}$ hydrocarbon, particularly to gasoline range C$_6$-C$_{10}$ hydrocarbon and hydrogen, using a bifunctional pentasil zeolite catalyst, having strong acid and dehydrogenation functions, at a temperature below 700° C.

However, since the co-reactants employed in the processes of the referenced patents are themselves valuable commodities, there is interest in developing alternative routes for the conversion of alkane, e.g., C$_{4-}$ alkane, such as methane, into C$_{5+}$ hydrocarbon such as aromatics. Processes which would allow more methane to be incorporated into an aromatic product are particularly desired.

Improvements in distribution of oxygen for carrying out the conversion of alkanes such as methane into C$_{5+}$ hydrocarbons are also desired. Additionally, reduction in undesired combustion reactions competing with the alkane conversion is desired.

SUMMARY OF THE INVENTION

This invention relates to a hydrocarbon conversion process that is less energy-intensive and has greater selectivity for the desired products than comparable processes. The hydrocarbon conversion process is particularly desirable for converting alkanes such as methane into C$_{5+}$ hydrocarbons, particularly with increased selectivity for aromatics-containing C$_{5+}$ hydrocarbon compositions. Additionally, the process lessens undesired combustion reactions that would otherwise compete with the desired conversion reaction.

In certain aspects, the invention relates to a process for producing a C$_{5+}$ composition. The process includes a step of providing a flow-through reactor comprising (i) a first hydrocarbon conversion catalyst having at least one of oxidative coupling functionality and oxydehydrogention functionality, (ii) a second hydrocarbon conversion catalyst having dehydrocyclization functionality, and (iii) an oxygen storage material. The flow-through reactor typically comprises thermal mass, e.g., thermal mass associated with one or more of the first hydrocarbon conversion catalyst, the second hydrocarbon conversion catalyst, and the oxygen storage material.

The reaction is carried out during at least two time intervals. During a first time interval, oxidant is passed through the flow-through reactor system, and at least a portion of the oxidant's oxygen is stored with the oxygen storage material, typically in or on the oxygen storage material or as part of the oxygen storage material's composition. The flow of oxidant through the flow-through reactor is lessened or discontinued.

During a second time interval, hydrocarbon reactant is passed through the flow-through reactor system, the hydrocarbon reactant comprising $C_{4-}$ hydrocarbon. At least a portion of the stored oxygen is released from the oxygen storage material, and the released oxygen reacts with at least a portion of the hydrocarbon reactant's $C_{4-}$ hydrocarbon in the presence of the first hydrocarbon conversion catalyst to produce a first reaction mixture comprising $C_{4-}$ olefin. At least a portion of the first reaction mixture's $C_{4-}$ olefin is catalytically converted in the presence of the second hydrocarbon conversion catalyst to produce a second reaction mixture comprising a $C_{5+}$ composition. At least a portion of the second reaction mixture is conducted away from the flow-through reactor system.

In particular aspects, the flow-through reactor comprises (i) a first hydrocarbon conversion catalyst having at least one of oxidative coupling functionality and oxydehydrogention functionality, (ii) a second hydrocarbon conversion catalyst having dehydrocylization functionality, (iii) an oxygen storage material, and (iv) thermal mass. During a first time interval, a flow of oxidant is introduced into the flow-through reactor, and at least a portion of the oxidant's oxygen is transferred to the oxygen storage material for storage. At least one of (i) the transferring of oxygen from the oxidant and (ii) the storing of the transferred oxygen with the oxygen storage material includes at least one exothermal reaction; and the process further comprises transferring at least a portion of the heat from the exothermal reaction to the thermal mass. The first flow is lessened or substantially halted. A second flow comprising methane is then transferred to the flow-through reactor. Additional heat is transferred to the thermal mass. At least a portion of the oxygen storage material's stored oxygen is released, and at least a portion of the released oxygen reacts with at least a portion of the second flow's methane in the presence of the first hydrocarbon conversion catalyst to produce ethylene. The reaction of the methane and the released oxygen is typically net exothermic, and at least a portion of any heat released from the exothermic reaction is transferred to the thermal mass. At least a portion of the ethylene reacts in the presence of the second hydrocarbon conversion catalyst to produce aromatics and molecular hydrogen. The reaction of the ethylene in the presence of the second hydrocarbon conversion catalyst is typically endothermic, and at least a portion of any heat needed by that reaction can be transferred to the reaction from the thermal mass.

In other aspects, the invention relates to a flow-through reactor for producing a $C_{5+}$ composition. The flow-through reactor comprising (a) a first region having a first thermal mass segment and a first aperture, (b) a second region having a second thermal mass segment and a second aperture, and (c) a catalytic conversion zone containing catalyst having (i) oxidative coupling functionality and/or oxydehydrogenation functionality and (ii) oxydehydrogenation functionality. At least one of the first and second thermal mass comprises oxygen storage material. The first and second regions are configured for flowing a feed mixture to enter the reactor proximate to the first aperture, with one or more components of a reaction mixture exiting the reactor proximate to the second aperture. The flow-through reactor can be a uni-flow or reverse-flow reactor. In another aspect, the invention relates to a system and method for producing $C_{5+}$ hydrocarbon, particularly aromatics, in the reactor.

Figure 1A:
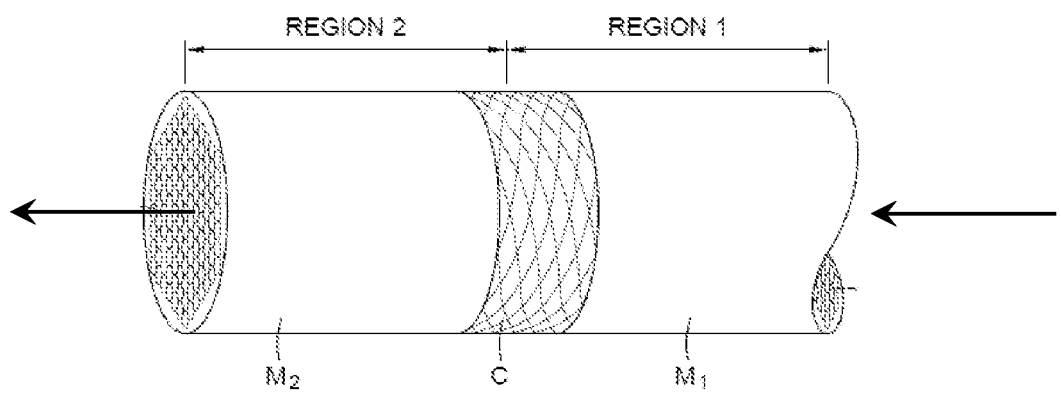
FIG. 1A is an example of a flow-through reactor, which includes a thermal mass, at least one oxygen storage material, and hydrocarbon conversion catalyst having at least (i) oxidative coupling functionality and/or oxydehydrogention functionality and (ii) dehydrocylization functionality.

Although the invention can be described in terms of hydrocarbon conversion processes, particularly oxygen storage/release processes and oxidative coupling reaction and/or oxydehydrogenation processes, for producing $C_{5+}$ hydrocarbons, the invention is not limited thereto. In other words, to the extent that the following detailed description is specific to a particular aspect or a particular use, the exemplary embodiments are intended to be illustrative only, and are not to be construed as limiting the scope of the invention. On the contrary, it is intended to cover all alternatives, modifications and equivalents that may be included within the spirit and scope of the invention.

DETAILED DESCRIPTION OF THE INVENTION

I. Introduction and Definitions

Certain aspects of the invention relate to reactors, systems, and reaction processes for contacting hydrocarbon reactant in the presence of oxygen stored and released from an oxygen storage material. The oxygen storage material can be one having thermal mass, or alternatively or in addition, can be located proximate to, on, or within a thermal mass located in at least one region of the reactor. Oxygen released from the oxygen storage material catalytically reacts with alkane, such as $C_{4-}$ alkane, e.g., methane, in the presence of a first hydrocarbon conversion catalyst comprising oxidative coupling catalyst and/or oxydehydrogention catalyst. The specified reaction produces a first reaction mixture comprising a $C_{5+}$ composition. While not wishing to be bound by any theory or model, it is believed that a part of the conversion process is a result of (i) one or more oxidative coupling reactions when the hydrocarbon reactant comprises methane and/or (ii) one or more oxydehydrogenation reactions when the hydrocarbon reactant comprises $C_{2+}$ alkane, with the conversion producing a first reaction mixture or first reaction product comprising $C_{2+}$ compositions, e.g., $C_{2+}$ olefins, e.g., $C_2$-$C_4$ olefin, such as ethylene. Another part of the conversion process is believed to entail catalytic conversion of at least a portion of the hydrocarbons in the first reaction mixture by dehydrocyclization reactions in the presence of a dehydrocyclization catalyst to produce a second reaction mixture or product comprising a $C_{5+}$ composition that can include a relatively high quantity of $C_6$ to $C_{10}$ aromatic compounds compared to comparable alkane conversion processes.

Oxygen storage and release for carrying out the catalytic conversion is achieved by including an oxygen storage material. In certain aspects, a thermal mass is utilized which comprises, consists essentially of, or consists of oxygen storage material. Oxygen is transferred from the oxidant to the oxygen storage material for storage with the oxygen storage material. Oxygen is typically transferred and stored as the oxidant is passed through the thermal mass region of the reactor. Oxygen can be transferred from the oxidant to the oxygen storage material for storage with the oxygen storage material can be in any form, e.g., as oxygen atoms, oxygen ions, or as a component of an oxygen-containing molecule (e.g., an oxygen precursor). Stored oxygen released from the oxygen storage material for reacting with the hydrocarbon reactant to produce the first reaction mixture can be in any form, e.g., as oxygen atoms, oxygen ions, or as a component of an oxygen-containing molecule (e.g., an oxygen precursor).

Storage of the oxygen can cause the thermal mass to be heated. For example, storage of the oxygen can be accompanied by exothermic reaction with the thermal mass. Thus, the oxidant itself can be considered a heating fluid for heating the flow-through reactor.

Alternatively or in addition, a hydrocarbon fuel can be included with the oxidant, e.g., as components of a heating fluid. The hydrocarbon fuel can be combusted to produce a combustion gas, with additional heat being transferred to the thermal mass. The heating fluid can contain oxygen at a stoichiometric excess for substantially complete combustion with the hydrocarbon fuel, and at least a portion of the oxygen from the oxidant can be transferred to the oxygen storage material for storage and subsequent release.

In certain aspects, the invention relates to a reaction system that includes a reactor comprising: (i) a first region having a first thermal mass segment and a first aperture; (ii) a second region having a second thermal mass segment and a second aperture, and (iii) a catalytic conversion zone containing a first catalyst having an oxidative coupling functionality, and a second catalyst having dehydrocyclization functionality with the conversion zone further including an oxygen storage material. Alternatively or in addition, the first catalyst can comprise an oxydehydrogenation functionality, which is particularly desired for hydrocarbon conversion of $C_{2+}$ alkane-containing feeds, e.g., $C_{4-}$ alkane-containing feeds, such as methane-containing feeds. At least a portion of the first catalyst, second catalyst and oxygen storage material can be deposited on or in the thermal mass, such as on or in at least one of the first thermal mass segment and second thermal mass segment. The first and second regions can be configured for flowing a first flow of an oxidant to enter the reactor proximate to the first aperture at a first time interval, and for flowing a first flow of a hydrocarbon reactant to enter the reactor proximate to the first aperture at a second time interval, with the first and second time intervals being at separate time intervals relative to one another. The first and second regions can be further configured to flow one or more components of a first reaction mixture to exit the reactor proximate to the second aperture.

Optionally, the reactor of the reaction system can be a reverse-flow reactor. For example, the reverse-flow reactor can be further configured for flowing a second flow of an oxidant, and a second flow of a hydrocarbon reactant to enter the reactor proximate to the second aperture. These second flows can also be at separate time intervals relative to one another, with the reactor further being configured to exit one or more components of a second reaction mixture proximate to the first aperture.

The invention is not limited to these aspects, and this description is not meant to foreclose the use of other reactors, other reactor components, other oxidants, and/or other hydrocarbon reactants within the broader scope of the invention. For the purpose of this description and appended claims, the following terms are defined:

The term "hydrocarbon" means compounds containing hydrogen bound to carbon, and encompasses (i) saturated hydrocarbon, (ii) unsaturated hydrocarbon, and (iii) mixtures of hydrocarbons, including mixtures of hydrocarbons (saturated and/or unsaturated) having different values of n.

The term "$C_n$" hydrocarbon wherein n is a positive integer, e.g., 1, 2, 3, 4, or 5, means hydrocarbon having n carbon atom(s) per molecule.

The term "$C_{n+}$" hydrocarbon wherein n is a positive integer, e.g., 1, 2, 3, 4, or 5, means hydrocarbon having at least n carbon atom(s) per molecule.

The term "$C_{n-}$" hydrocarbon wherein n is a positive integer, e.g., 1, 2, 3, 4, or 5, means hydrocarbon having no more than n number of carbon atom(s) per molecule.

The term "alkane" means substantially saturated compounds containing hydrogen and carbon only, e.g., those containing ≤1% (molar basis) of unsaturated carbon atoms. The term alkane encompasses $C_1$ to $C_5$ linear, iso, and cyclo alkanes.

The term "unsaturate" means a $C_n$ hydrocarbon containing at least one carbon atom directly bound to another carbon atom by a double or triple bond.

The term "aromatics" means hydrocarbon molecules containing at least one aromatic core.

The term "Periodic Table" means the Periodic Chart of the Elements, as it appears on the inside cover of The Merck Index, Twelfth Edition, Merck & Co., Inc., 1996.

The term "oxidant" means any oxygen-bearing material which, under the conditions in the reaction zone, yields oxygen for transfer to the oxygen storage material, for storage with and subsequent release from the oxygen storage material to the oxidative coupling and/or oxydehydrogenation. While not wishing to be limited to theory, molecular oxygen atoms may be provided as a reactive gas in a gaseous zone and/or atomic oxygen may be provided from a catalyst surface as, for instance, reacted, sorbed forms.

The term "oxidative coupling" refers to the oxygen-assisted dehydrogenation and coupling (formation of C—C bonds) of alkane (particularly methane) to produce water and hydrocarbon of higher order, such as producing $C_2$ hydrocarbon from methane. The term "oxydehydrogenation" means oxygen-assisted dehydrogenation of an alkane, particularly a $C_{2+}$ alkane, to produce an equivalent alkene and water without coupling.

The term "dehydrocyclization" means any process involving both dehydrogenation and cyclization of non-cyclic hydrocarbon, particularly $C_{2-}$ alkane, to produce a hydrocarbon having at least one cyclic structure. The cyclic structures can be saturated or unsaturated, with unsaturated structures including aromatic structures.

The term "hydrocarbon conversion catalyst" means any catalyst having at least one of oxidative coupling functionality, oxydehydrogenation functionality and dehydrocyclization functionality.

The term "residence time" means the average time duration for non-reacting (non-converting by oxidative coupling) molecules (such as He, $N_2$, Ar) having a molecular weight in the range of 4 to 40 to traverse the reactor or a defined zone within the reactor, such as a reaction zone of a oxidative coupling reactor.

The term "catalytic oxidative coupling reactor" means a reactor in which oxidative coupling and/or oxydehydrogenation reactions are carried out. In such reactions, ≥30.0% of the heat utilized by the reactions are provided by heat transfer from reactor components, e.g., solid surfaces associated with the reactor, such as tubulars or bed materials. In a thermal catalytic oxidative coupling reactor, ≥50.0% of the heat utilized by the reactions are provided by heat transfer from reactor components, optionally ≥80.0% or ≥90.0%. Optionally, an exothermic reaction (e.g., combustion) occurs within the catalytic oxidative coupling reactor, e.g., for preheating and/or reheating one or more components of the flow-through reactor, e.g., first and/or second thermal mass segments. Dehydrocyclization reactions can also be carried out in the catalytic oxidative coupling reactor.

The term "reaction stage" or "reactor stage" means at least one flow-through reactor, optionally including means for conducting one or more feeds thereto and/or one or more products away therefrom.

With respect to flow-through reactors, the term "region" means a location within the reactor, e.g., a specific volume within the reactor and/or a specific volume between a flow-through reactor and a second reactor, such as a second flow-through reactor. With respect to flow-through reactors, the term "zone", refers to a specific function being carried out at a location within the flow-through reactor. For example, a "reaction zone" or "reactor zone" is a volume within the reactor for conducting at least one of oxidative coupling, oxydehydrogenation and dehydrocyclization. Similarly, a "quench zone" or "quenching zone" is a location within the reactor for transferring heat from products of the catalytic hydrocarbon conversion, such as $C_{2+}$ olefin.

The term "flow-through reactor" refers to a reactor design in which feeds and/or reaction mixtures can flow through the reactor, e.g., where oxidant feeds, hydrocarbon reactant feeds, and/or reaction mixtures coming into contact with the first and/or second hydrocarbon conversion catalyst and/or oxygen storage material as the feeds and/or reaction mixtures flow through the reactor.

The term "tubular reactor" means an elongated, reactor vessel of substantially any cross-section, the vessel being configured to allow fluid flow into, though, and out of the vessel, via first and second apertures, the first and second apertures being located proximate to opposed ends of the elongated reactor vessel. With respect to flow-through reactors, the term "residence time" means the average time duration for non-reacting (non-converting by oxidative coupling) molecules (such as He, $N_2$, Ar) having a molecular weight in the range of 4 to 40 to traverse the flow-through reactor or a defined zone within the flow-through reactor, such as a reaction zone.

The term "fixed-bed catalytic reactor" means a catalytic reactor having at least one bed of catalyst, wherein the catalyst is substantially retained within the bed.

II. Reactor Apparatus and Process

The reaction for converting alkane to $C_{5+}$ hydrocarbon is carried out in at least one reactor. In the present disclosure, a reactor refers to equipment used for chemical conversion. As such, several items identified as reactors may be combined to become a single entity that is also identified as a reactor, in that individual and combined entities may be characterized as equipment used for chemical conversion.

The conversion of alkane to $C_{5+}$ hydrocarbon according to this convention involves oxidative conversion reactions, with the main oxidative conversion reactions being carried out in the reaction zone section of the reactor. When the hydrocarbon feed to the reactor comprises methane, the oxidative reactions include one or more of the following exothermic reactions:

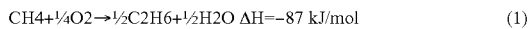  (1)

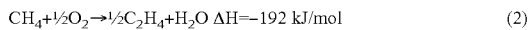  (2)

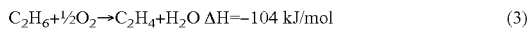  (3)

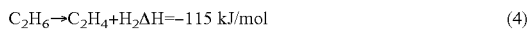  (4)

and optionally combustion, which consumes more oxygen and generates more heat:

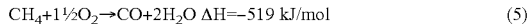  (5)

  (6)

It has been found that by regulating oxygen storage and the relative flow of reactant and oxidant, reactions (1)-(4) can be favored over reactions (5) and (6), and over reactions which combust one or more of the desired products. Such undesirable combustion reactions include $C_2H_x + O_2 \rightarrow CO_2 + H_2O$, such as $C_2H_4 + 3O_2 \rightarrow 2CO_2 + 2H_2O$ (−1412 kJ/mol) and $C_2H_6 + 7/2O_2 \rightarrow 2CO_2 + 3H_2O$ (−1517 kJ/mol). An advantage of the invention is that coke deposited during catalytic hydrocarbon conversion reactions can be removed from inside the reactor during a subsequent oxygen-storage step. It has been further found that a mixture comprising the hydrocarbon conversion products, particularly the products of the above reaction (1)-(4), can be further catalytically converted in the presence of a catalyst having dehydrocyclization functionality to produce $C_{5+}$ hydrocarbons.

The overall hydrocarbon conversion processes, i.e., (i) oxidative coupling reactions and/or oxydehydrogenation reactions and (ii) dehydrocyclization reactions are carried out in the presence of hydrocarbon conversion catalysts, and are believed to be catalytic processes. At least the oxidative coupling and/or oxydehydrogenation reactions are carried out in the presence of stored oxygen released from the oxygen storage material. The hydrocarbon conversion catalysts and oxygen storage material can be located in one or more thermal masses of the reactor, with the conversion reactions being carried out at temperatures and pressures effective for converting alkane to $C_{5+}$ hydrocarbon. For example, the hydrocarbon conversion processes are particularly efficient when carried out at reaction zone temperatures of from 550° C. to 1100° C. Alternatively, the overall hydrocarbon conversion process to produce the $C_{5+}$ hydrocarbon is particularly efficient at reaction zone temperatures of from 650° C. to 900° C., or at temperatures of from 675° C. to 825° C.

Operating pressures may include a pressure of at least atmospheric pressure (zero pressure, gauge), such as ≥4 pounds per square inch gauge (psig) (28 kilo Pascals gauge (kPag)), or ≥15 psig (103 kPag), or ≥36 psig (248 kPag), or ≥44 psig (303 kPag), or ≥103 psig (709 kPag), but may be ≤300 psig (2064 kPag), or ≤163 psig (1121 kPag), or ≤150 psig (1032 kPag).

Residence times in the reactor may be ≤20 seconds, ≤10 seconds and preferably ≤5 seconds or in the range of 0.01 seconds to 20 seconds or in the range of from 0.5 seconds to 10 seconds. For a reverse-flow reactor, the process may operate at cycle times≥0.5 second, such as in the range of 10 seconds to 240 seconds, in the range of 10 seconds to 120 seconds, in the range of 20 seconds to 60 seconds, or in the range of 20 seconds to 40 seconds. The term "cycle time" means the time from a first interval to the next first interval, including (i) intervening second, third, and/or fourth intervals and (ii) any dead-time between any pair of intervals.

Also, as may be appreciated, these different pressures and temperatures may be utilized together to form different combinations depending on the specific configuration of equipment.

Any flow through reactor can be used which is suitable for carrying out oxidative coupling reactions, oxydehydrogenation reactions and dehydrocyclization reactions. For example, fixed-bed catalytic reactors can be used. Examples of fixed-bed catalytic reactors include fixed-bed tubular reactors.

Flow-through type reactors are particularly suitable for carrying out (i) the oxidative coupling reactions and/or oxydehydrogenation reactions and (ii) the dehydrocyclization reactions. As a first step, or during a first time interval, oxidant is passed through the flow-through reactor. The flow-through reactor is maintained under conditions of temperature, pressure, and flow sufficient to transfer oxygen from the oxidant to the oxygen storage material and to store the transferred oxygen with the oxygen storage material. When additional heat is needed, this can be provided to the flow-through reactor by one or more of (i) heating the oxidant upstream of or in the flow through reactor, (ii) selecting the oxidant and/or oxygen storage material, and (iii) introducing a hydrocarbon fuel into the flow-through reactor with the oxidant to combust and exothermically release heat. When the oxidant provides heat to the flow-through reactor, the oxidant can be referred to as "heating fluid". Heating fluid can be utilized, e.g., when one or more of (i) the oxygen transfer and/or storage are net endothermic, (ii) the first catalytic hydrocarbon conversion, namely the oxidative coupling reactions and/or oxydehydrogenation reactions, is net endothermic, and (iii) the second catalytic hydrocarbon conversion, namely the dehydrocyclization of hydrocarbon in the first reaction mixture, is net endothermic (typically the case).

When the oxygen transfer/oxygen storage is net exothermic, oxygen is transferred from the oxidant to the oxygen storage mate to heat the thermal mass. Oxygen from the oxidant is stored with the oxygen storage material as the oxidant is passed through the reactor, with at least a portion of the heat produced during the oxygen transfer storage being transferred to the flow-through reactor, e.g., to the flow-through reactor's thermal mass. Oxidant flow is lessened or stopped after (i) sufficient oxygen is stored with the oxygen storage material for carrying out the specified first catalytic hydrocarbon conversion and (ii) sufficient heat is added (if any is needed) for carrying out the specified oxygen transfer/storage and the specified first and second catalytic hydrocarbon conversions.

During a subsequent or second time interval, hydrocarbon reactant is passed through the flow-through reactor under conditions of pressure, temperature and flow sufficient for releasing at least a portion of the oxygen that was transferred to and stored with the oxygen storage material during the first time interval. As the hydrocarbon reactant flows through the reactor, at least a portion of the hydrocarbon reactant reacts with at least a portion of the released oxygen in the presence of at least the first hydrocarbon conversion catalyst. When additional heat is needed for the reacting, one or more of (i) the type and/or amount of hydrocarbon reactant and (ii) the reacting conditions are selected so that the additional heat is released during at least part of the second time interval. For example, the flow-through reactor can configured to release weakly-bound stored oxygen proximate to the surface of the oxygen storage material, which weakly-bound oxygen then exothermically reacts with the hydrocarbon reactant. At least a portion of the heat released during this exothermic reaction can be transferred to the oxygen storage material to assist in the release of more tightly-bound stored oxygen within the oxygen storage material.

The reacting of the hydrocarbon reactant with the released oxidant in the presence of the first hydrocarbon conversion catalyst produces a first reaction mixture comprising (i) a $C_{2+}$ composition, (ii) water, and optionally (iii) molecular hydrogen. It is surprisingly found that the amount of stored oxygen released and reacted with the hydrocarbon reactant under the specified conditions is in a desired range for favoring reactions (1)-(4) over reactions (5) and (6), and over reactions which combust hydrocarbon in the reaction mixture.

Continued or subsequent contact of the first reaction mixture's $C_{2+}$ hydrocarbon, particularly $C_2$ to $C_4$ olefin, and more particularly ethylene, with the dehydrocyclization catalyst produces a second reaction mixture comprising the $C_{5+}$ hydrocarbon composition, and particularly a $C_{5+}$ hydrocarbon composition comprising aromatics.

The $C_{5+}$ hydrocarbon composition of the overall conversion process can comprise, e.g., (i) $\geq 5.0$ wt. % of $C_{5+}$ hydrocarbon, e.g., $\geq 10.0$ wt. %, such as $\geq 15$ wt. %; (ii) and $\leq 10.0$ wt. % $C_2$ to $C_4$ hydrocarbon, e.g., 5.0 wt. %, such as $\leq 1.0$ wt. %; the weight percents being based on the weight of the product. When the hydrocarbon reactant comprises methane, methane conversion can be generally $\geq 5.0$ wt. %, based on the weight of methane in the feed, e.g., $\geq 10.0$ wt. %, such as $\geq 15.0$ wt. %.

The $C_{5+}$ hydrocarbon product can comprise mainly aromatics, e.g., $\geq 50.0$ wt. % of $C_6$ to $C_{10}$ aromatics, based on the weight of the product's $C_{5+}$ hydrocarbon, such as $\geq 75.0$ wt. %, or $\geq 90.0$ wt. %, or $\geq 95.0$ wt. %. For example, when the hydrocarbon reactant comprises methane, the weight ratio of aromatic hydrocarbon produced to methane converted can be $\geq 0.5$, such as $\geq 0.1$.

The $C_6$ to $C_{10}$ aromatics can readily be removed from the $C_{5+}$ hydrocarbon product by any appropriate method. For example, the $C_6$ to $C_{10}$ aromatics can readily be removed from the $C_{5+}$ hydrocarbon product by one or more fractionation and extraction. Conventional methods can be used, but the invention is not limited thereto.

Oxidant and hydrocarbon reactant can be flowed in the same direction in the flow-through reactor ("uni-flow"), provided each flow is carried out during separate time intervals. For example, during a first time interval a heating fluid (e.g., pre-heated oxidant and/or oxidant heated in the flow-through reactor during the first time interval by combustion of a portion of the oxidant with a hydrocarbon fuel) can be flowed in a forward direction. During a second or subsequent time interval, the hydrocarbon reactant can be flowed in the forward direction through the flow-through reactor.

If desired, when the heating fluid includes an oxidant and hydrocarbon fuel, and a combustion gas is produced by oxidant combustion with a hydrocarbon fuel, a sweep fluid can be passed through the flow-through reactor to remove at least a portion any combustion gas that might remain within the reactor. The sweep fluid can be passed through the reactor during a time interval between the first time interval and the second time interval. The sweep fluid can be passed in the forward direction or the reverse direction. Typical sweep fluids include relatively inert liquids and vapors, especially those which are relatively easy to separate from the desorbed $C_{2+}$ composition. Steam and/or molecular nitrogen are examples of suitable sweep fluids.

The thermal mass of the flow-through reactor can comprise a first thermal mass segment and a second thermal mass segment. In such embodiments, during the second time interval, the first thermal mass segment can be heated and the second thermal mass segment can be cooled as the catalytic conversion is continued. Oxygen stored with the oxygen storage material can be endothermically released from the thermal mass during the second time interval, contributing to the cooling.

Reverse-flow catalytic reactors can be used to carry out the first and second catalytic hydrocarbon conversions, including one or more conventional reverse-flow reactors. Reactors typically used for converting or cracking reactions, and to execute cyclic, high temperature chemistry, can be used, such as those described in U.S. Pat. Nos. 7,943,808, 7,491,250, 7,846,401, and 7,815,873.

Generally, forward and reverse flows through reverse-flow catalytic reactors are carried out during separate time intervals. For example, the heating fluid can be flowed in a first or forward direction through the reverse-flow reactor, during a first time interval. During a second or subsequent time interval, the hydrocarbon reactant can be flowed in a second or reverse direction through the reverse-flow reactor.

Reverse-flow catalytic reactor cycles typically are either symmetric or asymmetric. Asymmetric cycles are typically used to execute endothermic reactions (e.g., dehydrocyclization), and the desired endothermic reaction is paired with a different reaction that is net exothermic (e.g., combustion of hydrocarbon fuel in the heating fluid and net exothermic oxygen transfer/storage in connection with the oxygen storage material) to provide heat of reaction for the endothermic reaction.

Regenerative, reverse-flow catalytic oxidative coupling reactors can be used to carry out (i) the oxidative coupling and oxydehydrogenation reactions and (ii) the dehydrocyclization reactions. A regenerative, reverse-flow reactor is (i) "reverse flow" in the sense that an upstream region of the reactor with respect to the average flow of the first feed mixture corresponds to the downstream region with respect to the average flow of the second feed mixture and (ii) "regenerative" in the sense that at least a portion of any heat lost (e.g., by radiation) during a time interval is restored by heat released during a subsequent interval (and vice versa). For example, combusting at least a portion of the heating fluid's hydrocarbon fuel with a portion of the heating fluid's oxidant can provide heat to the reverse-flow reactor's thermal mass during the first time interval. Heat can be withdrawn from the thermal mass to when the combination of first and second catalytic hydrocarbon conversion reactions is net endothermic, which can substantially restore the reverse-flow reactor's temperature profile to that subsisting at the start of the first time interval. The first and second time intervals can then be repeated, one after the other. Hydrocarbon deposits formed during the specified first and/or second hydrocarbon conversions (e.g., coke deposits in the reverse-flow reactor) during the second time interval, can be removed by combustion with a portion of the heating fluid's oxidant during a subsequent first time interval. This can lessen the amount of hydrocarbon fuel needed in the heating fluid, and can substantially prevent the accumulation of hydrocarbon deposits in the reverse-flow reactor. Heat can be transferred to and stored with the reverse-flow reactor during the first and second time intervals, e.g., by transferring heat within a defined volume (e.g., the first and/or second thermal mass segments).

A variety of flow-through reactors are suitable. The flow-through reactor can be physically symmetric, e.g., a reverse-flow reactor that is symmetric about a central axis. The flow-through reactor can be adiabatic, e.g., an adiabatic reverse-flow reactor. The flow-through reactor can include a housing, a plurality of flow-control means (e.g., conduits and valves), one or more insulation components (e.g., insulation bricks) and one or more process flow components (e.g., thermal mass, mixing components, etc.). The housing may be utilized to enclose an interior region and has one or more insulation components disposed adjacent to the housing. The plurality of flow control means may include one or more conduits, one or more apertures, and one or more valves that are configured to manage the flow of one or more streams into and out of the interior region from a location external to the interior region or housing. Process flow components can be configured and/or arranged to manage the flow of fluids through the interior region, wherein the one or more process flow components may include a thermal mass having different portions with each having different flow passages and a wetted area. In embodiments where the first and/or second mixtures are combined in a reverse-flow reactor, one or more mixer or mixer-distributors can be used for the mixing.

Regenerative reverse-flow reactors may involve multiple steps repeated in sequence to form a cycle for the process. For example, the process can include two or more sequential steps, such as two or more steps operated continuously in sequence (one step after the other). The steps can include, e.g., (i) a net endothermic, forward-flow hydrocarbon conversion step, (ii) a net exothermic, reverse-flow, oxygen transfer/storage and reactor regeneration step, (iii) a repetition of the forward-flow hydrocarbon conversion step, and (iv) a repetition of the reverse-flow oxygen transfer/storage and reactor regeneration step. The steps may involve passing mixtures over a solid material in fixed orientation (e.g., one or more thermal masses). As part of these steps, valves may be utilized to alternate introduction of feed mixtures into the reactor, e.g., a first feed mixture comprising hydrocarbon reactant and a second feed mixture comprising oxidant-containing heating fluid.

As an example, regenerative reactors can deliver a heating fluid comprising hydrocarbon fuel and oxidant, with the oxidant's oxygen content being at a stoichiometric excess for substantially complete combustion with the hydrocarbon fuel, directly to a location along the flow path within the reactor (e.g., a mixing zone). At least a portion of the heating fluid's hydrocarbon fuel combusts, transferring heat to the flow-through reactor, e.g., to the reactor's thermal mass. The combustion reaction can be carried out to heat the thermal masses before, during and/or after one or more intervals of the oxidative coupling reaction. For example, a combustion reaction can be carried out to initially heat (e.g., preheat) one or more thermal masses of the reverse-flow reactor. Combustion products can then be exhausted using a sweep fluid. A flow of sweep fluid can be established during the same time interval as which the heating fluid flow is established through the flow-through reactor, or alternatively or in addition, during a subsequent time interval occurring before (or during) which a flow of hydrocarbon reactant through the flow-through reactor is established. Following reactor regeneration and oxygen transfer/storage, the hydrocarbon reactant flow is established through the reactor. Hydrocarbon reactant is exposed to the reactor's heated thermal mass, and heat can be transferred between the thermal mass and the hydrocarbon reactant for (i) releasing oxygen stored with the oxygen storage material and (ii) the catalytic reaction of the hydrocarbon reactant with the released oxygen, to produce the first reaction mixture. Further heat can be transferred between the first reaction mixture and the reactor's thermal mass (or a segment thereof) for reacting the first reaction mixture's $C_{2+}$ hydrocarbon (e.g., ethylene) in the presence of the second hydrocarbon conversion catalyst (the dehydrocyclization catalyst). A second reaction product, produced by catalytic dehydrocyclization reaction, can be quenched, if needed, by additional thermal mass (or an additional thermal mass segment) located in the flow-through reactor. The quenching can be accomplished, e.g., by transferring heat to a cooler region of the reactor, obviating the need for an external quench as in conventional processes. For example, the reactor can contain a cooler thermal mass (a second thermal mass or segment of the thermal mass that is cooler than the second reaction mixture) located downstream of the first and second catalytic hydrocarbon conversion reactions. In operation, the second thermal mass segment absorbs heat from the second reaction mixture during a time interval (during hydrocarbon reactant flow), sufficient to (i) cool the product mixture to quench the reaction and (ii) impart heat to the heating fluid (when the flow is reversed) during a subsequent time interval.

The reactor may include reactor components, such as process flow components (e.g., reactor components used to manage the flow of mixtures through the reactor, one or more of the thermal masses for absorbing, storing and releasing heat, catalyst, sorbent, and/or mixing component) and insulation components (e.g., reactor components used to manage the heat transfer from the process flow within the reactor to the external surface of the reactor, such as insulation bricks, tiles or packing). The reactor components may be formed from different materials, such as refractory support materials, which can be used to support the catalyst and sorbent.

Heat generated during one or more the conversion step, e.g., one or more of (i) oxygen transfer/storage, the first catalytic hydrocarbon conversion, and (iii) the second catalytic hydrocarbon conversion can be stored in a thermal mass material. The thermal mass material is one that is designed or adapted to facilitate storage and utilization of heat. One or more of the oxygen storage material, the first hydrocarbon conversion catalyst, and the second hydrocarbon conversion catalyst can be utilized as thermal mass. Additional thermal mass can be associated with the flow-through reactor if needed, e.g., in cases where the insufficient thermal mass is provided by the oxygen storage material, the first hydrocarbon conversion catalyst, and the second hydrocarbon conversion catalyst.

The thermal mass typically comprises material (e.g., a solid material) that can transfer (e.g., absorb, store, and release) thermal energy over a temperature range for carrying out the reverse flow cycle, which includes the oxidative coupling reaction and any optional combustion reaction. For example, the thermal mass can be a solid material that can absorb, release, and store heat from reactants and products over a temperature range in which oxidative coupling can be carried out, including those that do so without any significant phase change. In particular embodiments, the solid material can absorb and store heat and release the stored heat, without any significant phase change, over a temperature range in which oxidative coupling and hydrocarbon combustion are carried out. Examples of temperature ranges at which the thermal mass absorbs, stores and releases thermal energy include a range of from 50° C. to 1500° C., alternatively from 100° C. to 1500° C. or from 200° C. to 1500° C. The thermal mass can be characterized by one or more properties. Examples of such properties include melting temperature, porosity, bulk density, thermal conductivity, thermal expansion and thermal capacity.

Melting temperatures (melting points) are reflective of the ability of the thermal mass to withstand combustion and oxidative coupling temperatures without chemical change and/or physical destruction. Thermal masses having higher melting points are preferred according to this invention. For example, the melting point of the thermal mass of this invention is preferably at least 1200° C., or at least 1500° C.

Porosity is a measure of the effective open pore space in the thermal mass into which heat and gasses can penetrate and eventually degrade the structure. The porosity of a thermal mass can be expressed as the average percentage of open pore space in the overall refractory volume. As an example, the thermal masses utilized in certain embodiments of this invention can have a porosity of not greater than 50%, or not greater than 40%, or not greater than 30%. The porosity can be measured by an Archimedes process, e.g., mercury porosimitry.

Bulk density is a measure of the weight of a given volume of the thermal mass. Higher bulk densities, with lower porosities, can be particularly effective. As an example, the thermal masses utilized in certain embodiments of this invention can have a bulk density of at least 0.5 g/cm$^3$. For example, the bulk density can be from 0.5 g/cm$^3$ to 3.5 g/cm$^3$ or from 1 g/cm$^3$ to 3 g/cm$^3$.

Thermal conductivity is defined as the quantity of heat that will flow through a unit area in direction normal to the surface area in a defined time with a known temperature gradient under steady state conditions. Thermal conductivity represents a general heat flow characteristic of the thermal mass. Typical thermal masses have a relatively high thermal conductivity. For example, the thermal mass can have a thermal conductivity of from 0.1 W/mK to 50 W/mK or from 0.2 W/mK to 30 W/mK.

Thermal expansion of the thermal mass should not be so great such that cracking of the material occurs during operation of the reaction system. In one aspect, the thermal mass can be characterized by a thermal expansion coefficient. For example, the thermal mass can have a thermal mass coefficient of from $0.1 \times 10^{-6}$/K to $20 \times 10^{-6}$/K or from $0.2 \times 10^{-6}$/K to $15 \times 10^{-6}$/K. In this example, the thermal expansion coefficient is given as a value in a temperature range of from 25° C. to 800° C.

Thermal capacity is the ability of a material to hold heat. The thermal masses utilized in certain embodiments of this invention preferably has a higher thermal capacity, but not so high as to increase the probability of cracking at higher temperatures. For example, the thermal masses utilized in certain embodiments of this invention can have a thermal capacity of from 250 Jm$^3$/K to 4500 Jm$^3$/K or from 500 Jm$^3$/K to 3000 Jm$^3$/K.

Checker bricks, tiles, and monoliths may be used as to form the thermal mass components within the reactor. Such materials form a network of passages that are used by the gases in each step to transit the region containing solid material. The thermal mass may be a ceramic, which may include yttria, zirconia, alumina, and/or other refractory material capable of adsorbing, storing and transferring heat, and that are effective in withstanding temperatures within the oxidative coupling reactor.

In certain embodiments, one or more of the thermal masses includes separate passages through reactor components to manage the flow of hydrocarbon components and or oxidant through the thermal mass. Preferably, each thermal mass includes separate passages. The separate flow passages in the thermal mass can further comprise flow barriers that effectively function as walls to lessen or prevent cross flow or mixing of fluids (e.g., reactants, oxidants, and/or products) between passages, except in the desired regions of the reactor. Each thermal mass preferably includes a plurality of passages (called "channels"), which may preferably be in parallel flow arrangement. The channeled thermal mass may preferably be comprised of one or more honeycomb monoliths. Preferred honeycomb monoliths are structures that comprise many (e.g., a plurality, meaning more than one) fluid-flow passages, arranged in parallel fashion with walls serving to separate each passage. Such reactor can include a single monolith or a plurality of monoliths. Each monolith can be formed by extruding or die pressing monolith blocks with shaped (e.g., square or hexagonal) cross-section and two- or three-dimensionally stacking, such blocks above, behind, and beside each other. Monoliths are particularly effective as thermal mass because they provide high heat transfer capacity with lessened pressure drop.

The thermal mass may include (i) a first portion comprising a first plurality of flow passages (a first channel) and having a first wetted area $a_{v1}$; and (ii) a second portion comprising a second plurality of flow passages (a second channel) and having a second wetted area $a_{v2}$, wherein (i) $a_{v1} \neq a_{v2}$ and (ii) $a_{v2}$ is different from $a_{v1}$ by at least 25%. The difference percentage for $a_v$, as used herein, is defined to be based on the higher of the two wetted areas. For example, if $a_{v1} \geq a_{v2}$, then the percent difference between $a_{v1}$ and $a_{v2}$ is $100*(a_{v1}-a_{v2})/a_{v1}$.

III. Oxygen Storage Material

The reactor includes at least one oxygen-storage material, namely a material having functionality for transferring at least a portion of the oxidant's oxygen, storing the transferred oxygen, and releasing at least a portion of the stored oxygen under the specified conditions. The oxygen storage material can be a material having oxygen-sorptive capacity, as well as the ability to release the sorbed oxygen, particularly at elevated temperatures. The oxygen storage material can comprise a metal oxide, for example a transition metal oxide, having a reversible sorptive affinity for oxygen at elevated temperature. Such materials include those that sorptively remove and release oxygen from oxidant and those that undergo a chemical and/or physical change in the course of reversible oxygen storage.

As used herein, the term "elevated temperature" means a temperature in the range of from 400° C. to 1000° C. As used herein, the term "high sorptive capacity" means an oxygen storage capacity of at least 40 millimoles of oxygen per mole of the oxygen storage material that contacts the oxidant at a temperature of 800° C.

The oxygen storage material can be utilized as materials mixed with or coated onto a support or substrate. For example, the oxygen storage material can be utilized as finely divided materials as a part of a thermal mass or as one or more coatings on a thermal mass substrate to provide a material having oxygen-storage functionality.

A thermal mass comprising material having oxygen-storage functionality can be used to temporarily store an oxygen at relatively high temperatures for use in the overall catalytic hydrocarbon conversion reactions to produce the specified $C_{5+}$ reaction mixture. For certain oxygen storage materials, as the temperature of the thermal mass is lessened, oxygen is more easily transferred to the oxygen storage material. In other oxygen storage materials, as the temperature of the thermal mass is lessened, oxygen is more easily released from the oxygen storage material. Heat transfers needed for (i) transferring and/or storing oxygen and (ii) for the specified hydrocarbon conversion reactions can include the transfer of heat to/from the reactor's thermal mass.

In certain aspects, a thermal mass comprising oxygen storage material is heated to a relatively high temperature. As oxidant contacts the heated thermal mass over a first time interval, oxygen is transferred to and stored with the oxygen storage material. During a second time interval, hydrocarbon can be contacted with stored oxygen released from the heated oxygen storage material, with the hydrocarbon being further heated by the heated thermal mass. As the heated hydrocarbon and released oxygen contact the first hydrocarbon conversion catalyst, at least a portion of the hydrocarbon (e.g., methane) is catalytically converted to produce a first reaction mixture. Although the hydrocarbon conversion reaction can be exothermic, release of the oxygen under continued contact and reaction with the hydrocarbon can be carried out under overall (net) endothermic conditions. This means that oxygen can be more readily released over time, as the release of the oxygen and reaction with the hydrocarbon will ultimately decrease thermal mass temperature. This decrease in temperature gradually eases oxygen release from the oxygen storage material, which lessens the amount of combustion of hydrocarbon reactant with released oxygen that would otherwise occur.

In certain aspects, the oxygen storage material can enable the bulk separation and purification of oxygen based on ionic transport, in which the oxygen storage material is maintained at high temperature to temporarily store oxygen. Oxygen that contacts the surface of the oxygen storage material can be decomposed on the surface of the material and incorporated into the crystalline lattice of the material. Storage of the oxygen can be particularly facilitated over the temperature range from 400° C. to 1000° C. A featured of the process is that oxygen transfer, storage, and release can be carried out continuously under the specified process conditions without appreciable decomposition of the oxygen storage material.

In certain aspects, when oxidant contacts the oxygen storage material, oxygen in the oxidant can be adsorbed and dissociated, with charge transfer acting to cause penetrative flux of the oxygen species into the oxygen storage material. A chemical potential driving force can be employed to effect ionic transport of the oxygen species into the oxygen storage material.

The transfer of oxygen to the oxygen storage material and the storage of the oxygen with the oxygen storage material can be net exothermic. In these cases, these reactions can transfer heat to the substrate material such as the thermal mass. When the oxygen storage material is a component of a thermal mass, the oxygen storage material can be coated onto, mixed with, or otherwise associated with the thermal mass.

The oxygen storage material can be of any suitable size, shape and conformation appropriate to oxygen storage and conversion of hydrocarbon. For example, the material can be in a finely divided form, e.g., beads, spheres, rings, toroidal shapes, irregular shapes, rods, cylinders, flakes, films, cubes, polygonal geometric shapes, sheets, fibers, coils, helices, meshes, sintered porous masses, granules, pellets, tablets, powders, particulates, extrudates, cloth or web form materials, honeycomb matrix monolith, composites (of the oxygen storage material with hydrocarbon conversion catalyst and/or thermal mass), including in comminuted or crushed forms.

In certain embodiments, the oxygen storage material can be formed by metal-organic chemical vapor deposition (MOCVD) on suitable supports or substrates, e.g., thermal masses, using appropriate precursors for the respective metal components of the oxygen storage material. Use of MOCVD allows relatively close control of stoichiometry and uniformity of coverage to be achieved. MOCVD can be used to deposit films of multicomponent oxygen storage materials with compositional reproducibility on the order of 0.1% and thickness uniformity of better than 5%.

Alternatively, the oxygen storage material can be formed as bulk articles, e.g., particles, by various manufacturing techniques. Such techniques include powder metallurgy, slurry metallurgy (slip casting, tape casting, etc.) and coextrusion.

Another alternative technique for forming the oxygen storage material can be a sol gel technique. Such technique can be advantageous when the oxygen storage material is deposited on an inert substrate, such as a thermal mass comprising porous silica, alumina, kieselguhr, or the like. Sol gel techniques can be employed to make up a sol of the precursor constituents of the oxygen storage material and to spray, dip-coat, soak, roller coat, or otherwise apply the solution to the substrate, e.g., the thermal mass. The coated substrate containing the precursor material can be subjected to high temperature, e.g., calcined, to produce the desired oxygen storage material.

Transition metal oxides are particularly useful as oxygen storage materials. Transition metals can be considered an IUPAC Group 3-12 element and elements of the Lanthanide series. Preferred oxygen storage materials can be oxides containing at least one Group 3, Group 6, Group 7, Group 8, Group 9 and Lanthanide series element. Examples of each these metals are shown in the Periodic Table.

Perovskites and related materials, such as perovskite-like materials and pyrochlores, can be particularly useful as oxygen storage materials. "Perovskites" can generally be considered oxygen-containing compounds having the crystal structure, $ABO_3$, with high-temperature $O^{2-}$ vacancies. Such structures can also be denoted by use of the symbol δ, according to the general formula $ABO_{3-\delta}$. The "A"-site cations can be rare earth (e.g., Lanthanide series including La and Y), alkaline earth (i.e., Group 2), alkaline (Group 1) and large cations such as $Pb^{2+}$, $Bi^{3+}$, or $Ce^{4+}$. The "B"-site cations can be 3d, 4d, or 5d transition-metal cations. Multiple cation-type occupations are possible. Framework sites "A" and "B" can be dodecahedral and octahedral, respectively, cf., L. G. Tejuca and J. L. Fierro, *Properties and Applications of Perovskite-type Oxides*, Marcel Dekker, New York, 1993.

A standard cubic high-temperature perovskite phase can remain stable and reversible with regard to changes of δ within a certain range: The value δ can be up to 0.25; for example δ can be from 0.05 to 0.25 (although higher values have been reported), at elevated temperature and low oxygen partial pressure, i.e., δ is a function of temperature and partial pressure of oxygen. Perovskite stability can be governed by cation radii of lattice metals in various valence states combined into a parameter "t" called "tolerance factor", cf., Z. Shao, et al., *Sep. Purif Technol.*, 25 (2001) 419-42. A perovskite structure can be formed at t ranges from 0.75-1.

Examples of useful perovskites and perovskite structures can be found in U.S. Pat. No. 7,338,549. Such examples include, but are not limited to, those having the general formulas (1), (2), and (3):

$$A_xB_yO_{3-\delta}, \quad (1)$$

$$A_xA'_{x'}B_yB'_{y'}O_{3-\delta}, \quad (2)$$

$$A_xA'_{x'}A''_{x''}B_yB'_{y'}B''_{y''}O_{3-\delta}, \quad (3)$$

and combinations thereof, wherein:

A, A', and A" are independently selected from ions of atoms having atomic number ranging from 57-71, inclusive, a cation of yttrium, ions of Group 1 atoms, ions of Group 2 atoms, and combinations of two or more, where Group 1 and Group 2 refer to the periodic table of elements;

B, B', and B" are independently selected from d-block transition-metal ions selected from Mn, Cr, Fe, Co, Ni, and Cu;

x, x', x", y, y', and y" are each real numbers ranging from 0 to 1.0; and x+x'+x"=0.8–1.0; y+y'+y"=1.0; and δ ranges from about 0.05 to about 0.30.

Perovskite-like compounds useful in the invention are those having general formulas (4), (5), (6), (7), (8), and (9):

$$A_2BO_{4-\delta} \quad (4)$$

$$A_2B_2O_{5-\delta} \quad (5)$$

$$AO(ABO_{3-\delta})_n \quad (6)$$

$$AM_2Cu_3O_{7-\delta} \quad (7)$$

$$Bi_4V_{2(1-x)}Me_{2x}O_{11-3x}, \quad (8)$$

$$A''B''O_3 \quad (9)$$

wherein: A is independently selected from ions of atoms having atomic numbers ranging from 57-71, inclusive, a cation of yttrium, ions of Group 1 atoms, ions of Group 2 atoms, and combinations of two or more, where Group 1 and Group 2 refer to the periodic table of elements;

B is independently selected from d-block transition metal ions;

A" is an ion of Na or Li, and B" is an ion of W or Mo;

M is a metal cation selected from cations of Group 2 atoms of the periodic table of elements;

Me is a metal cation selected from cations of Cu, Bi, and Co atoms;

x is a real number ranging from 0.01 to 1.0;

n ranges from 1 to about 10; and

δ ranges from about 0.05 to about 0.30.

Pyrochlores useful in the invention are those having general formula (10):

$$A_2B_2O_{7-\delta} \quad (10)$$

wherein: A is independently selected from ions of atoms having atomic numbers ranging from 57-71, inclusive, a cation of yttrium, ions of Group 1 atoms, ions of Group 2 atoms, and combinations of two or more, where Group 1 and Group 2 refer to the periodic table of elements;

B is independently selected from d-block transition metal ions; and

δ ranges from about 0.05 to about 0.30.

Cerium-containing and praseodymium-containing metal oxides can also be used as the oxygen storage material. Examples of such materials include $CeO_2$, $Pr_6O_{11}$, $CeO_2$—$ZrO_2$, $CuO$—$CeO_2$, $FeO_x$—$CeO_2$ (1.0≤X≤1.5), $MnO_x$—$CeO_2$ (1.0≤X≤3.5), and $Pr_6O_{11}$—$CeO_2$.

In certain embodiments, at least a portion of one or more of the thermal masses can include material having oxygen-storage functionality as well as catalytic functionality. Such thermal masses are referred to herein as thermal masses comprising a catalyst composite.

Various arrangements of materials having oxygen-storage functionality and materials having catalytic functionality are contemplated. For example, the catalyst composite can be a mixed metal oxide comprising: 1) a first metal oxide having catalytic functionality for (i) oxidative coupling functionality and/or oxydehydrogenation functionality and (ii) dehydrocyclization functionality and 2) a second metal oxide having oxygen storage functionality. First and second metal oxides can be located proximate to thermal mass (e.g., in or on passages of a honeycomb monolith open to the flow of oxidant and hydrocarbon reactant), or may themselves function as thermal mass.

A first metal oxide having catalytic functionality for (i) the first catalytic hydrocarbon conversion reaction (oxidative coupling functionality and/or oxydehydrogenation functionality) and (ii) the second catalytic hydrocarbon conversion reaction (dehydrocyclization functionality) can be arranged as catalyst particles, such as in a physical mixture of catalyst particles. Additional thermal mass, if needed can be included in the mixture, or (alternatively or in addition) the catalyst particles can be deposited on a thermal mass material. The second metal oxide having oxygen storage functionality can also be included with the physical mixture of catalyst and/or thermal mass; e.g., in a mixture with the thermal mass without catalyst; alternatively deposited on the thermal mass.

For example, in certain aspects, the flow-through reactor includes at least one composite, the composite comprising oxygen storage material, the first hydrocarbon conversion catalyst, and the second hydrocarbon conversion catalyst. In certain aspects, the composite comprises one or more molecular sieve-containing catalysts specified for the second hydrocarbon conversion catalyst. Oxygen storage material and first hydrocarbon conversion catalyst can be located in pores of the molecular sieve, e.g., as dispersed particles located within zeolite pores. The particles can be uniformly dispersed, e.g., with particles of oxygen storage material dispersed substantially uniformly among particles of the first hydrocarbon conversion catalyst, but this is not required. The particles can be substantially uniformly dispersed throughout the pores of the second hydrocarbon conversion catalyst's molecular sieve, but this is not required, and in some aspects it is advantageous for at least the oxygen storage material particles to be located near one or more pore openings of the molecular sieve. Conventional methods can be used for depositing oxygen storage material particles and/or first hydrocarbon conversion catalyst particles in the molecular sieve's pores, e.g., one or more of chemical impregnation, ion exchange, and chemical vapor deposition, but the invention is not limited thereto. The composite can be in the form of a honeycomb monolith having at least one channel for establishing the specified flows of oxidant and hydrocarbon reactant.

In other aspects, the composite is a physical mixture of oxygen storage material, first hydrocarbon conversion catalyst, and second hydrocarbon conversion catalyst. The composite can comprise additional thermal mass if needed. The catalyst composite can be a staged composite. A "staged composite" is a catalyst composite in which the composite's components are situated in a particular order with respect to the established flows. For example, the oxygen storage material can be located between the first hydrocarbon conversion catalyst and the second hydrocarbon conversion catalyst, with the second hydrocarbon conversion catalyst being located proximate to the established flows. A stage can comprise two components, e.g., a first stage comprising the second hydrocarbon conversion catalyst and a second stage comprising a combination of first hydrocarbon conversion catalyst and oxygen storage material. The first stage is typically located proximate to the established flows. The stages can be arranges in layers, e.g., the composite can be in the form of a layered composite. In one layered composite, the composite is located in at least one channel of a honeycomb monolith. The innermost layer (proximate to the established flows) comprises the second hydrocarbon conversion catalyst. The outermost layer comprises the first hydrocarbon conversion catalyst. A third layer located between the inner and outer layer comprises oxygen storage material.

It was expected that such a layered composite would exhibit the best performance because hydrocarbon reactant (e.g., methane) was expected to transit the first layer largely unaffected by the second hydrocarbon conversion catalyst. The transited methane would then react with released oxygen from the oxygen storage material as desired, in the presence of the first hydrocarbon conversion catalyst. The first reaction product (e.g., ethylene), transiting the first layer would react as desired with the second hydrocarbon conversion catalyst, with the second reaction product ($C_{5+}$ hydrocarbon) then being transferred to the channel. It has been found that the performance of such a layered composite is exceeded by a composite comprising oxygen storage material and first hydrocarbon conversion catalyst located in pores of the second hydrocarbon conversion catalyst's molecular sieve (a molecular sieve composite). While not wishing to be bound by any theory or model, it is believed that the enhanced performance of the molecular sieve composite results from two features: (i) heat made available by the typically net exothermic reaction of released oxygen with hydrocarbon reactant readily transfers to the second hydrocarbon conversion catalyst to provide heat for the typically endothermic dehydrocyclization reaction and (ii) molecular hydrogen made available by the dehydrocyclization reaction can react with released oxygen from the oxygen storage material located in the pores of the dehydrocyclization catalyst's molecular sieve to produce water, which debottlenecks the dehydrocyclization reaction in the molecular sieve's pores by consuming a dehydrocyclization product (molecular hydrogen).

IV. Catalyst Having Oxidative Coupling Functionality and/or Oxydehydrogenation Functionality Hydrocarbon conversion catalysts useful in carrying out at least a portion of the reactions for producing $C_{5+}$ hydrocarbon compositions include a first hydrocarbon conversion catalyst effective in converting alkane (e.g., $C_{4-}$ alkane, such as methane) in the presence of oxygen released form the oxygen storage material to produce a first reaction mixture comprising a $C_{2+}$ composition (e.g., $C_2$ to $C_4$ olefin, such as ethylene). Hydrocarbon conversion catalysts particularly useful as first hydrocarbon conversion catalysts include oxydehydrogenation catalysts and oxidative coupling catalysts, such as metal oxide hydrocarbon conversion catalysts useful in oxydehydrogenation and oxidative coupling reactions. The metal oxide catalysts also include mixed metal oxide catalysts, meaning that there may be more than one metal element in the oxide catalyst. Particularly useful metal oxide catalysts are metal oxide catalysts effective in catalytically converting alkane (e.g., methane) to $C_{2+}$ compositions, particularly $C_{2+}$ olefin (e.g., ethylene).

An effective metal oxide catalyst can include at least one base metal of IUPAC Group 2, Group 3, Group 7, Group 8, Group 9, Group 14, Group 15 and the lanthanide series of metals. The metal oxide catalyst can additionally include at least one Group 1 metal. Examples of each these metals are shown in the PERIODIC CHART OF THE ELEMENTS, The Merck Index, 12$^{th}$ Ed., Merck & Co., Inc., 1996 ("Periodic Table").

Examples of Group 1 metals include Li, Na, K, Rb, Cs and Fr. Li, Na, K, Rb and Cs represent more common Group 1 metals.

Examples of Group 2 metals include Be, Mg, Ca, Sr, Ba and Ra. Mg, Ca, Sr and Ba are more common Group 2 metals.

Examples of Group 3 metals include Sc, Y, La and Ac. La is an example of a particularly common Group 3 metal.

Examples of Group 7 metals include Mn and Re. Mn is an example of a particularly common Group 7 metal.

Examples of Group 8 metals include Fe, Ru and Os. Fe is an example of particularly common Group 8 metal.

Examples of Group 9 metals include Co, Rh and Ir. Co is an example of particularly common Group 9 metal.

Examples of Group 14 metals include Sn and Pb. Pb is an example of a particularly common Group 14 metal.

An example of a Group 15 metal includes Bi.

Examples of the lanthanide series of metals include Ce, Pr, Nd, Sm, Eu, Gd, Tb, Dy, Ho, Er, Tm, Yb and Lu. Sm, Gd, Ho, and Yb are more common lanthanide metals.

Specific examples of oxidative coupling catalysts include those listed in U.S. Pat. No. 6,096,934. Such catalysts include lithium supported on magnesium oxide where the lithium is present in either the hydroxide or oxide form; bismuth supported on calcium oxide where the bismuth is present in either the hydroxide or oxide form; lithium supported on calcium oxide where the lithium is present in either the hydroxide or oxide form; cerium supported on magnesium oxide where the cerium is present in either the hydroxide or oxide form; nickel and lanthanum supported on magnesium oxide where the lanthanum is present in either the hydroxide or oxide form and the nickel is present in the metallic form; and lithium supported on lanthanum oxide where the lithium is present in either the hydroxide or oxide form; or any other metal or metal oxide or hydroxide catalyst promoted with a Group 1, 2, or lanthanide series element present in an oxide or hydroxide form.

U.S. Pat. No. 5,245,124 discloses an order of oxidative coupling catalysts first reported by Y. A. Amenomiya et al. in "Conversion of Methane by Oxidative Coupling," report to CANMET, Energy, Mines and Resources, Ottawa, Canada. The rating of catalysts is listed as follows: $Li/Sm_2O_3$>Na/CaO>K/CaO>$LaAl_2O_3$>$Sm_2O_3$>Li/CaO>PbO>$Bi_2O_3$>$Ho_2O_3$>$Gd_2O_3$>Li/MgO>Li/CaO~$Yb_2O_3$>$Y_2O_3$Na/MgO~CaO>MgO. Additives to the catalysts include Ba, Li, Sr, Pb, K, Mg, Ca, Na, and Sb.

Perovskites of the structure $A_2B_2C_3O_{10}$ are also useful as catalysts for the oxidative coupling and/or oxydehydrogenation of lower alkane to heavier hydrocarbons. A is alkali metal; B is lanthanum or a lanthanide element, for example, cerium, neodymium, samarium, praseodymium, gadolinium or dysprosium; and C is titanium. A particular example is shown in U.S. Pat. No. 5,026,945, in which the perovskite is represented by the formula $A_xLn_yTi_zO_{10}$, wherein A is one or more alkali metal; Ln is one or more of lanthanum, cerium, neodymium, samarium, praseodymium, gadolinium and dysprosium; x is about 2; y is about 2; and z is about 3.

The catalysts can be incorporated with the thermal mass of the reactor in a configuration in the hydrocarbon reactant flowing through the flow-through reactor and oxygen released from the oxygen storage material of the reactor are contacted in the presence of the hydrocarbon conversion catalyst to convert alkane in the hydrocarbon reactant to $C_{5+}$ hydrocarbons. The catalyst is preferably arranged along with one or more of the thermal masses of the reactor to transfer heat to the hydrocarbon reactant as it passes through the flow-through reactor. For example, the catalyst (and/or components thereof) can be arranged at one or more surfaces of the thermal masses adjacent to or mixed with the oxygen storage material, and in a manner in which hydrocarbon reactant passes over or across the catalyst and released oxygen. It has been observed that some of the materials which are suitable for use as the specified hydrocarbon conversion catalyst are also suitable for use as oxygen storage material. Such "dual-use" materials include those hydrocarbon conversion catalysts which (i) have two or more oxidation states and (ii) which are capable of oxygen uptake and release under the specified oxygen transfer conditions without substantial decomposition. Perovskite is an example of a "dual use" material.

V. Catalyst Having Dehydrocyclization Functionality

Hydrocarbon conversion catalysts useful as the second hydrocarbon conversion catalyst for producing a second reaction product comprising $C_{5+}$ hydrocarbon compositions (e.g., aromatics) can be any hydrocarbon conversion catalyst effective in converting $C_{2+}$ hydrocarbons (e.g., $C_2$ to $C_4$ olefins, such as ethylene) through a dehydrocyclization reaction.

In certain aspects, the invention relates to processes which include contacting the specified first reaction mixture with a bi-functional catalyst comprising at least one molecular sieve and at least one dehydrogenation component to produce the second reaction product. The second reaction product comprises, e.g., ≥5.0 wt. % of aromatics based on the weight of the product. It is believed that at least a portion of the first reaction product's hydrocarbon (e.g., the portion comprising olefin such as ethylene) is activated at the metal and acid sites of the bi-functional catalyst allowing the hydrocarbon, particularly $C_{2+}$ aliphatic hydrocarbon that may be present, to be aromatized at temperatures below 700° C., e.g., at a temperature≤300° C. The presence of unconverted oxygen released from the oxygen storage material during or in connection with the first catalytic hydrocarbon conversion reaction may assist in this activation, particularly when the released oxygen is included in oxygen-containing molecules such as oxygenate, and particularly alcohol.

The second hydrocarbon conversion catalyst is typically bi-functional, e.g., it is one having both dehydrogenation and cyclization functionalities. Representative bi-functional catalysts contain at least one acidic functionality (generally provided by a molecular sieve component) and at least one dehydrogenation functionality (generally provided by a dehydrogenation metal component). Certain catalysts useful in the invention will now be described in more detail. The invention is not limited to these catalysts, and this description is not meant to foreclose other catalysts within the broader scope of the invention.

In certain aspects, the second hydrocarbon conversion catalyst comprises at least one medium pore size molecular sieve having a Constraint Index of 2-12 (as defined in U.S. Pat. No. 4,016,218). Examples of such medium pore molecular sieves include ZSM-5, ZSM-11, ZSM-12, ZSM-22, ZSM-23, ZSM-35, ZSM-48 and mixtures and intermediates thereof. ZSM-5 is described in detail in U.S. Pat. Nos. 3,702,886 and Re. 29,948. ZSM-11 is described in detail in U.S. Pat. No. 3,709,979. A ZSM-5/ZSM-11 intermediate structure is described in U.S. Pat. No. 4,229,424. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231. Optionally, the molecular sieve is one comprising at least one set of pores of substantially uniform size extending through the molecular sieve, wherein geometric mean of the cross-sectional dimensions of each of the pores is >5 Å, or >5.3 Å, e.g., ≥5.4 Å such as ≥5.5 Å, or in the range of 5 Å to 7 Å, or 5.4 Å to 7 Å.

In other aspects, the catalyst employed as a second hydrocarbon conversion catalyst in the present process comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

(i) molecular sieves made from a common first degree crystalline building block unit cell, which unit cell has the MWW framework topology. (A unit cell is a spatial arrangement of atoms which if tiled in three-dimensional space describes the crystal structure.) Such crystal structures are discussed in the "Atlas of Zeolite Framework Types", Fifth edition, 2001, the entire content of which is incorporated as reference;

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as a molecular sieve component of the present catalyst.

In certain aspects, the molecular sieve employed in the present processes may be an aluminosilicate or a substituted aluminosilicate in which part of all of the aluminum is replaced by a different trivalent metal, such as gallium or indium.

The second hydrocarbon conversion catalyst can include such specified catalyst that has been subjected to one or more catalyst treatments, e.g., selectivation. For example, the second hydrocarbon conversion catalyst can comprise at least one molecular sieve which has been selectivated, either before introduction of the catalyst into the reactor or in-situ in the reactor, by contacting the catalyst with a selectivating agent, such as at least one organosilicon in a liquid carrier and subsequently calcining the catalyst at a temperature of 350 to 550° C. This selectivation procedure can be repeated two or more times and alters the diffusion characteristics of the catalyst such that the formation of paraxylene over other xylene isomers is favored. Such a selectivation process is described in detail in U.S. Pat. Nos. 5,633,417 and 5,675,047, the entire contents of which are incorporated herein by reference.

In addition to the molecular sieve component, the second hydrocarbon conversion catalyst generally comprises at least one dehydrogenation component, e.g., at least one dehydrogenation metal. The dehydrogenation component is typically present in an amount of at least 0.1 wt. %, such as from 0.1 to 5 wt. %, of the overall catalyst. The dehydrogenation component can comprise one or more neutral metals selected from Groups 3 to 13 of the Periodic Table of the Elements, such as Ga, In, Zn, Cu, Re, Mo, W, La, Fe, Ag, Pt, Pd, and/or one or more oxides, sulfides and/or carbides of these metals. The dehydrogenation component can be provided on the catalyst in any manner, for example by conventional methods such as impregnation or ion exchange of the molecular sieve with a solution of a compound of the relevant metal, followed by conversion of the metal compound to the desired form, namely neutral metal, oxide, sulfide and/or carbide. Part or all of the dehydrogenation metal may also be present in the crystalline framework of the molecular sieve. A carbonyl conversion functionality can also be used when the co-reactant comprises inorganic oxygenate, e.g., one or more of Cu, Co, Cr, Fe, Mo, Zn, such as in one or more of metal, oxide, sulfide, etc.

In one aspect, the bi-functional catalyst used as a second hydrocarbon conversion catalyst in the present process is selected from the group consisting of Ga and/or In-modified ZSM-5 type zeolites such as Ga and/or In-impregnated H—ZSM-5, Ga and/or In-exchanged H—ZSM-5, H-gallosilicate of ZSM-5 type structure and H-galloaluminosilicate of ZSM-5 type structure. These zeolites can also be prepared by any suitable method, including conventional methods.

For example, the second hydrocarbon conversion catalyst may be a bi-functional catalyst that contains tetrahedral aluminum and/or gallium, which is present in the zeolite framework or lattice, and octahedral gallium or indium, which is not present in the zeolite framework but present in the zeolite channels in close vicinity to the zeolitic protonic acid sites, and which is attributed to the presence of tetrahedral aluminum and gallium in the catalyst. The tetrahedral or framework Al and/or, Ga is responsible for the acid function of the catalyst and octahedral or non-framework Ga and/or In is responsible for the dehydrogenation function of the catalyst. In one preferred aspect, the bi-functional catalyst comprises H-galloaluminosilicate of ZSM-5 type structure having framework (tetrahedral) Si/Al and Si/Ga mole ratios of about 10:1 to 100:1 and 15:1 to 150:1, respectively, and non-framework (octahedral) Ga of about 0.5 to 0 wt. %.

In addition to the molecular sieve components and dehydrogenation component, the second or dehydrocyclization catalyst may be composited with another material which is resistant to the temperatures and other conditions employed in the conversion reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

VI. Reactor Feed Compositions

A first feed stream to the flow-through reactor includes oxidant (optionally as a heating fluid or a component thereof), which can be passed to the flow-through reactor at a first time interval. A second feed stream to the flow-through reactor includes hydrocarbon reactant, which can be passed to the flow-through reactor at a second time interval.

When the oxidant is contained in heating fluid, the heating fluid can be any oxygen-containing fluid that is (i) capable of transferring oxygen from the heating fluid to the oxygen storage material for storage with the oxygen storage material and (ii) capable of transferring heat to the flow-through reactor, such as transferring heat to the thermal mass of a flow-through reactor. The transfer can be through direct or indirect heat transfer between the heating fluid and the thermal mass. The heat transfer can include exothermal reaction, which produces heat that is transferred to the thermal mass.

The oxidant typically comprises one or more fluids which yield oxygen for the specified transfer/storage under the specified oxygen transfer/storage conditions. Typically, the oxidant includes one or more of molecular oxygen ($O_2$), $O_2^-$, $O_2^=$, ionized oxygen atoms, nitrogen oxides such as $N_2O$, etc. Oxidant is typically in the vapor phase at the specified hydrocarbon conversion conditions, but this is not required, and in certain aspects liquid and/or solid oxidant can be used. The oxidant can comprise $O_2$, e.g., ≥90% $O_2$ (molar basis, per mole of oxidant), such as, ≥99%. For example, the oxidant can comprise $O_2$ in air, or $O_2$ obtained or derived from air, e.g., by separation. The oxidant can comprise (or consist essentially of, or consist of) $O_2$ air. When the oxidant comprises $O_2$ in air, the total feed during the oxidant transfer/storage interval generally comprises at least a portion of the air's molecular nitrogen as diluent. In other words, when the oxidant comprises molecular oxygen in air, other gasses in the air, such as molecular nitrogen, are considered to be diluent, and are not considered to be part of the oxidant.

In alternative embodiments, the heating fluid further comprises hydrocarbon fuel. Hydrocarbon fuel can be considered any hydrocarbon or hydrocarbon mixture effective in carrying out a combustion reaction to release heat and produce combustion products such as carbon monoxide, carbon dioxide, water and combinations thereof. The heating fluid preferably contains oxygen from the oxidant at a stoichiometric excess for substantially complete combustion with the hydrocarbon fuel, and at least a portion of the oxidant (i.e., oxygen) is stored with the oxygen storage material. Examples of suitable hydrocarbon fuels include natural gas mixtures, other petroleum alkane-containing mixtures, petroleum distillates, kerosene, jet fuel, fuel oil, heating oil, diesel fuel and gas oil, gasoline, and alcohols. The hydrocarbon fuel can be selected from among the same compositions as the hydrocarbon reactant. For example, the hydrocarbon fuel can be of the same composition as the hydrocarbon reactant and/or can be obtained from the same source.

In certain embodiments, the oxidant comprises molecular oxygen ($O_2$). For example, the oxidant can comprise ≥90.0 wt. % of $O_2$, e.g., ≥99.0 wt. % of $O_2$, based on total weight of the oxidant. The $O_2$ can be $O_2$ in air, or $O_2$ obtained or derived from air, e.g., by separation. Nitrogen obtained or derived from air can be utilized as a feed mixture diluent.

In certain embodiments, the hydrocarbon reactant comprises alkane, e.g., $C_{4-}$ alkane. The alkane can comprise one or more $C_1$ to $C_4$ linear, iso, and cyclo alkanes. Specific examples include methane, ethane, propane, butane and pentane. Particular examples include methane, ethane and propane, with methane being a preferred alkane.

The hydrocarbon reactant can comprise ≥80 wt. % alkane, or ≥85 wt. % alkane, or ≥90 wt. % alkene, based on total weight of the hydrocarbon reactant. For example, the hydrocarbon reactant can comprise ≥80 wt. % methane, or ≥85 wt. % methane, or ≥90 wt. % methane, based on total weight of the hydrocarbon reactant, with the remainder of the hydrocarbon in the hydrocarbon reactant comprising one or more of $C_2$ to $C_4$ linear, iso, and cyclo alkane. Such a hydrocarbon reactant can also be used as the hydrocarbon fuel component of a heating fluid, if desired.

The feed streams (e.g., the heating fluid and/or the hydrocarbon reactant) can be diluted, e.g., with one or more diluents such as one or more inert materials. For example, the feed streams can be diluted with essentially inert fluid. Examples of inert fluid include, but are not limited to, steam, nitrogen, carbon dioxide or other fluids that are substantially unreactive with the hydrocarbon in the feed streams. When diluted, the diluent can provide from 5 wt. % to 80 wt. % of the feed streams, or from 10 wt. % to 50 wt. %, based on total weight of the feed streams. Dilution can be carried out by adding diluent to one or more of the reactant (alkane component of the feed stream), the oxidant, or the mixed reactant, and oxidant.

VII. Examples

Figure 1B:
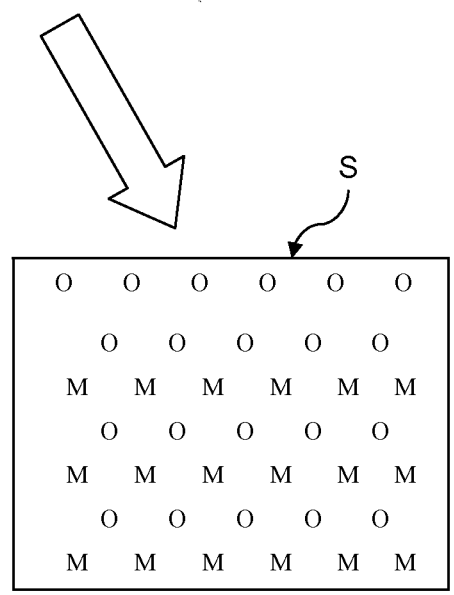
FIG. 1B is a simplified sectional enlargement of a reaction of the thermal mass, in which "M" refers to a metal center, representative of at least one oxygen storage material, and "O" refers to oxygen from an oxidant, which has been stored with the thermal mass.

With Reference to FIGS. 1A and 1B

Certain embodiments of the invention are depicted in FIGS. 1A and 1B. FIG. 1A illustrates a flow-through reactor, for example a catalytic reverse-flow reactor having a first region (Region 1) and a second region (Region 2), with the first and second regions comprising thermal mass.

The invention, however, is not limited to catalytic reverse-flow reactors having two regions, and the FIG. 1A description is not intended to foreclose other configurations of thermal mass. For example, the thermal mass material may be coupled together as a continuous mass in a single region or more than one region or separate thermal masses coupled together, forming more than one region. As another example, the thermal mass can be a continuous mass of a ceramic material having catalytic functionality (i.e., includes catalyst having one or more of oxidative coupling functionality, oxydehydrogenation functionality, and dehydrocyclization functionality) and oxygen-storage functionality (i.e., includes an oxygen storage material). In such a case, the thermal mass would be a multi-functional thermal mass.

The terms first and second thermal mass segments are used for convenience in FIG. 1A to particularly describe the heating and cooling of the regions of the thermal mass as the catalytic reactions progress through the flow of the feeds and conversion products through the reactor. The reaction being carried out results in absorption and release of heat in a manner that is effective in the continuous catalytic conversion of alkane in the hydrocarbon reactant feed to produce a reaction mixture comprising $C_{5+}$ compositions, particularly $C_6$ to $C_{10}$ aromatics.

The reactor in FIG. 1A includes a continuous thermal mass, which is represented as a first thermal mass segment M1 and a second thermal mass segment M2, with the thermal mass including a Reaction Zone C. The Reaction Zone C comprises at least one oxygen storage material and at least one hydrocarbon conversion catalyst having one or more of oxidative coupling functionality, oxydehydrogenation functionality, and dehydrocyclization functionality, which can be incorporated on or in either or both of the thermal mass segments M1 and M2 of the Reaction Zone C. For example, all of the oxygen storage material and hydrocarbon conversion catalyst can be incorporated in or on either thermal mass segment M1 or thermal mass segment M2 or a portion of the oxygen storage material and/or hydrocarbon conversion catalyst can be incorporated in or on both thermal mass segment M1 and thermal mass segment M2.

In an embodiment, at least a portion of the oxygen storage material and at least a portion of an oxidative coupling catalyst can be deposited on or in the first thermal mass segment M1 and/or the second thermal mass segment M2 of the Reaction Zone C. In another embodiment, at least a portion of the oxygen storage material, at least a portion of an oxidative coupling catalyst, and at least a portion of a dehydrocyclization catalyst can be deposited on or in the first thermal mass segment M1 and/or the second thermal mass segment M2 of the Reaction Zone C. In yet another embodiment, at least a portion of the oxygen storage material, at least a portion of a first hydrocarbon conversion catalyst having oxidative coupling and oxydehydrogenation functionality and at least a portion of a second hydrocarbon conversion catalyst having dehydrocyclization functionality can be deposited on or in the first thermal mass segment M1 and/or the second thermal mass segment M2 of the Reaction Zone C.

The oxygen storage material and hydrocarbon conversion catalyst in the Reaction Zone C can overlap both Region 1 and Region 2. However, the oxygen storage material and the hydrocarbon conversion catalyst can be completely located in either Region 1 or Region 2, and/or in a region located between Regions 1 and 2. The oxygen storage material and hydrocarbon conversion catalyst can be part of or attached to the thermal mass material of Region 1, Region 2, or both. Optionally, the oxygen storage material and hydrocarbon conversion catalyst can be located in a defined sub-region of the first and/or second thermal mass segment, the sub-regions being proximate to the center of the reactor as shown in FIG. 1A.

In a particular embodiment, (i) $\geq 10.0$ wt. % of a first hydrocarbon conversion catalyst (based on total weight of the first hydrocarbon catalyst in the reactor) and $\geq 10.0$ wt. % of a first oxygen storage material can be located on (or in) the first thermal mass segment M1, such as in a region proximate to a downstream end of the first thermal mass segment M1 (downstream being with respect to the flow of feeds); and (ii) $\geq 10.0$ wt. % of a second hydrocarbon conversion catalyst (based on total weight of the second catalyst in the reactor) can be located on (or in) the second thermal mass segment M2 and $\geq 10.0$ wt. % of a second oxygen storage material can be located on (or in) the second thermal mass segment M2, such as in a region proximate to a downstream end of the second thermal mass segment M2 (downstream being with respect to the flow of the feeds). The first and second hydrocarbon catalysts can be the same or different. The first and second oxygen storage materials can be the same or different.

In a particular embodiment, the first thermal mass segment M1 can comprise: 1) a first hydrocarbon conversion catalyst having at least one of oxidative coupling functionality and oxydehydrogenation functionality and 2) a first oxygen storage material, with the second thermal mass segment M2 comprising: 1) a second hydrocarbon conversion catalyst having dehydrocyclization functionality and 2) a second oxygen storage material.

In an embodiment, the flow-through reactor comprises: (a) a first region having a first thermal mass segment and a first aperture, (b) a second region having a second thermal mass segment and a second aperture, and (c) a catalytic conversion zone containing a first hydrocarbon conversion catalyst having an oxidative coupling functionality, oxydehydrogenation functionality or both, a second hydrocarbon conversion catalyst having an dehydrocyclization functionality, and an oxygen storage material, with at least a portion of the first hydrocarbon conversion catalyst, second hydrocarbon conversion catalyst and oxygen storage material being deposited on or in at least one of the first thermal mass and second thermal mass segments. The first and second regions are configured for flowing a feed mixture to enter the reactor proximate to the first aperture, with one or more components of a reaction mixture exiting the reactor proximate to the second aperture.

In an alternative embodiment, the reactor is a reverse-flow reactor, which comprises: (a) a thermal mass, which comprises a first region having a first thermal mass segment and a first aperture, and a second region having a second thermal mass segment and a second aperture; (b) a first catalyst having an oxidative coupling functionality, oxydehydrogenation functionality or both; (c) a second catalyst having an dehydrocyclization functionality; and (d) an oxygen storage material. The components of the reverse-flow reactor are further configured such that i. $\geq 50.0$ wt. % of the first catalyst, based on total weight of the first catalyst, is located on or in the first thermal mass segment of the first region, ii. $\geq 50.0$ wt. % of the oxygen storage material, based on total weight of the oxygen storage material is located on or in the first thermal mass segment of the first region, and iii. $\geq 50.0$ wt. % of the second catalyst, based on total weight of the catalyst, is located on or in the second thermal mass segment of the second region. The first and second regions are further configured for flowing a feed mixture to enter the reactor proximate to the first aperture of the first region, with one or more components of a reaction mixture exiting the reactor proximate to the second aperture of the second region.

FIG. 1B is a characterization of a cross-sectional enlargement of the Reaction Zone C. "M" of FIG. 1B refers to a metal center, representative of at least one oxygen storage material and at least one hydrocarbon conversion catalyst. "O" of FIG. 1B refers to an oxidant such as oxygen, which has been stored in the Reaction Zone C from a first process step in which heating fluid comprising an oxidant is flowed through the reactor.

As seen in FIG. 1B, oxygen from the oxidant can be stored in a portion of the thermal mass of the reaction zone containing oxygen storage material M. As the oxidant is flowed through the reactor, at least a portion of the oxidant (i.e., oxygen) is stored with the oxygen storage material. The oxygen can migrate from the surface S of the thermal mass toward a more central region of the thermal mass, becoming more deeply embedded in the thermal mass. As flow of oxidant continues, the storage of oxygen can reach a maximum or saturation-type level. The oxygen at the surface S of the thermal mass is more loosely bound to the oxygen storage material than the oxygen at the oxygen embedded further inwardly. Thus, the surface oxygen (depicted as the O's above the dotted line of FIG. 1B) is more easily released. This can be a particular advantage in heat balance at the beginning of a reaction process. For example, excess oxygen at the surface means that the reaction process can be more easily initiated. Thus, less energy can be used to carry out the overall reaction process.

As the hydrocarbon reactant is flowed through the reactor, the stored oxygen is released, catalytically reacting with the alkane in the hydrocarbon reactant to produce a reaction mixture comprising a $C_{2+}$ composition. The $C_{2+}$ composition can then be converted in the presence of the hydrocarbon conversion catalyst having dehydrocyclization functionality to produce the $C_{5+}$ composition.

The oxygen storage material and hydrocarbon conversion catalyst in the thermal mass of Reaction Zone C do not need to be in any particular order or arrangement. Enough of each material is present to the extent that the thermal mass containing the materials exhibits oxygen storage functionality or capacity and catalytic functionality for the conversion reaction.

An example of the process for producing a $C_{5+}$ composition can be described with reference to FIG. 1A. During a first step of the process for producing the $C_{5+}$ composition, or during a first time interval, heating fluid comprising an oxidant is passed through the flow-through reactor to heat the thermal mass in a forward direction, as shown by the direction of the arrow. Oxygen from the oxidant is stored with the oxygen storage material in Reaction Zone C as the oxidant is passed through the reactor, with heat produced during the oxygen storage being transferred to the thermal mass. Storage of the oxygen with the oxygen storage material can involve or include at least one exothermal reaction, causing heat to be generated, with heat transfer being carried out through storage of the oxygen with the oxygen storage material in Reaction Zone C. The heating fluid can further comprise a hydrocarbon fuel. In such instance, the heating fluid is passed through the flow-through reactor under combustion conditions to produce a combustion gas. Heat from the combustion is also transferred to throughout the thermal mass to further heat the thermal mass. When the heating fluid comprises hydrocarbon fuel in combination with oxidant, it is preferred that the heating fluid contain the oxygen from the oxidant at a stoichiometric excess for substantially complete combustion with the hydrocarbon fuel. Over a desired cycle time, the flow of the heating fluid is stopped.

Following the heating of the thermal mass, i.e., during a second time interval, a hydrocarbon reactant comprising ≥10.0 wt. % alkane (e.g., methane), based on total weight of the hydrocarbon reactant, is passed through the flow-through reactor. As the reactant flows through the reactor, it passes across or through Reaction Zone C, with at least a portion of the alkane in the heated hydrocarbon reactant being converted, in the presence of oxygen stored in the oxygen storage material and a hydrocarbon conversion catalyst having at least one of oxidative coupling functionality and oxydehydrogenation functionality, to a first reaction mixture comprising a $C_{2+}$ composition. At least a portion of the first reaction mixture is then converted to a second reaction mixture comprising a $C_{5+}$ composition, with the conversion to the second reaction mixture being carried out in the presence of a hydrocarbon conversion catalyst having dehydrocylcization functionality. The second reaction mixture can be conducted away from the reactor for further processing, such as separation of $C_6$ to $C_{10}$ aromatics in the $C_{5+}$ composition.

The heating fluid and hydrocarbon reactant can be flowed in the same direction (i.e., a forward direction as shown by the arrow of FIG. 1A) as long as the flows are at separate time intervals. For example, the heating fluid can be flowed in a forward direction through the flow-through reactor, during a first time interval. During a second or subsequent time interval, the hydrocarbon reactant also can be flowed in the forward direction through the flow-through reactor.

The flow-through reactor of FIG. 1A can be operated as a reverse-flow reactor, with the oxygen-storage step being carried out in a first time interval and the catalytic conversion step being carried out in a second time interval. When the process is carried out in a reverse-flow arrangement, heating fluid and hydrocarbon reactant are flowed in opposite directions through the reverse-flow reactor at separate time intervals.

As shown in FIG. 1A, the heating fluid is flowed in a first or forward direction through the flow-through reactor, during a first time interval. When the flow-through reactor is operated in a reverse-flow arrangement, during a second or subsequent time interval, the hydrocarbon reactant is flowed in a second or reverse direction of the arrow shown in FIG. 1A.

The first and second time intervals, as generally described according to the exemplary scheme shown in FIG. 1A, can be substantially non-overlapping intervals. Each of the first and second time intervals can be, independently, an interval having a duration in the range of from about 0.5 seconds to about 15 seconds. The interval between the first and second time intervals (the "dead-time", which represents the interval of time it takes to reverse flow of the feed mixtures) is preferably as short as possible so that the reverse flow cycle can be as rapid as possible. From a practical standpoint, the dead-time should be, e.g., ≤ than 0.5 seconds, such as in a range of from about 0.01 seconds to about 0.5 seconds. Upon completion of the second time interval, the intervals can be repeated. That is, the flow shown in FIG. 1A can be reinitiated and followed by subsequent re-initiation of the flow shown in FIG. 1A.

A sweep fluid can be passed through the catalytic reverse-flow reactor after the oxygen storage step and/or after the catalytic conversion step. For example, a sweep fluid can be used during a third time interval to remove at least a portion of a combustion gas and/or unconverted heating fluid that might remain within the reactor between the first time interval and the second time interval. The sweep fluid can be passed in the forward direction or the reverse direction. The sweep fluid can be an inert fluid. Examples of inert fluids include, but are not limited to, steam, nitrogen, carbon dioxide or other fluids that are substantially unreactive with any hydrocarbon that may be present in the reactor.

As a particular example in which the heating fluid further comprises a hydrocarbon fuel, the heating fluid can be passed through the flow-through reactor, at a first time interval, under combustion conditions to produce a combustion gas, with heat being transferred from the combustion gas to the thermal mass. After the first time interval, i.e., during a second time interval, a sweep fluid can be passed through the flow-through reactor to remove at least a portion the combustion gas.

As another example, during a third time interval, a hydrocarbon reactant can be passed through the flow-through reactor to contact the thermal mass heated during the first time interval. The heated thermal mass can heat the hydrocarbon reactant, and the heated hydrocarbon reactant can be catalytically converted in the presence of the hydrocarbon conversion catalyst the stored oxygen to a reaction mixture comprising a $C_{2+}$ composition. After the third time interval, i.e., during a fourth time interval, additional sweep fluid can be passed through the flow-through reactor to remove at least a portion the reaction mixture.

In the exemplary embodiment shown in FIGS. 1A and 1B, the oxidant can comprise ≥90.0 wt. % of $O_2$, e.g., $O_2$ obtained from air, based on total weight of the oxidant. The hydrocarbon reactant can comprise ≥80 wt. % methane.

The invention is not limited to embodiments shown only in the FIGS. 1A and 1B. For example, in other embodiments, the flow-through reactor can comprise a honeycomb monolith in the form of an elongated polygonal body. The honeycomb can comprise two or more portions, the portions being in side-to-side contact, with each section having one or more flow passages feeding into a flow passage in the adjacent portion. That is, the portions can be adjacent to each other, with each upstream of the mixing means or each downstream of the mixing means.

In other embodiments, the reactor stages can include three, four, five, six or more thermal masses, each thermal mass having one or more than one reaction zone. The reactor zones in the reactor stages can be adjacent to each other or may optionally have a mixing means (e.g., mixing components or a gap) disposed between the portions.

As another example, the thermal mass or a portion of the thermal mass can comprise honeycomb monoliths. Monoliths that have straight channels can be utilized to minimize pressure drop and enable greater reactor length. Preferred honeycomb monoliths can have channel densities that range from about 1 cell/cm$^2$ to 250 cells/cm$^2$.

Further, the thermal mass can include various bed packing, which may have different wetted areas. That is, the bed packing may include one or more of monoliths, pebble beds, tiles and/or combinations of different bed packings. For instance, a monolith can be disposed adjacent to a pebble bed and/or other particulate packing, which may have a different wetted area.

In another embodiment, a foam monolith or packed bed can be utilized. These packings can be configured to provide a tortuous flow passage and have pore densities in the range of about 1 pore/cm to 20 pore/cm. In yet another embodiment, tiles may be utilized.

While the present invention has been described and illustrated with respect to certain embodiments, it is to be understood that the invention is not limited to the particulars disclosed and extends to all equivalents within the scope of the claims. Unless otherwise stated, all percentages, parts, ratios, etc. are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:

1. A process for producing a C5+ composition, comprising:
   (a) providing a reverse-flow reactor comprising: (i) first and second hydrocarbon conversion catalysts, the first hydrocarbon conversion catalyst having oxidative coupling functionality and the second hydrocarbon conversion catalyst having dehydrocyclization functionality and (ii) at least one thermal mass, wherein (A) the first hydrocarbon conversion catalyst, (B) the second hydrocarbon conversion catalyst, and (C) the oxygen storage material are deposited on or in the thermal mass, and within a catalytic conversion zone of the reverse-flow reactor;
   (b) during a first time interval,
   i. passing a heating fluid comprising an oxidant and a hydrocarbon fuel through the reverse-flow reactor system and a first portion of the oxidant with the hydrocarbon fuel under combustion conditions to (A) produce a heated combustion gas and (B) transfer heat from the heated combustion gas to the thermal mass, wherein the oxidant is present in the heating fluid in a stoichiometric excess of that needed for substantially complete combustion with the hydrocarbon fuel,
   ii. transferring at least a second portion of the oxidant's oxygen to an oxygen storage material for storage with the oxygen storage material, and
   iii. lessening or discontinuing the passing of the oxidant through the reverse-flow reactor;
   (c) during a second time interval,
   i. passing a hydrocarbon reactant comprising methane through the reverse-flow reactor,
   ii. releasing stored oxygen and catalytically converting at least a portion of the hydrocarbon reactant's methane with at least a portion of the released oxygen in the presence of the first hydrocarbon conversion catalyst to produce a first reaction mixture comprising a $C_{2+}$ composition, and
   iii. catalytically converting at least a portion of the first reaction mixture in the presence of the second hydrocarbon conversion catalyst to produce a second reaction mixture comprising the $C_{5+}$ composition; and
   (d) conducting at least a portion of the second reaction mixture away from the reverse-flow reactor.

2. The process of claim 1, wherein the heat transfer of step (b) (i) is carried out during the storage of oxygen with the oxygen storage material.

3. The process of claim 1, wherein oxidant stored with the oxygen storage material is endothermically released during the second time interval.

4. The process of claim 1, wherein the oxygen storage material comprises metal oxide.

5. The process of claim 4, wherein the metal oxide comprises perovskite.

6. The process of claim 1, wherein (i) the oxidant comprises ≥90.0 wt. % of $O_2$, based on total weight of the oxidant, and (ii) the hydrocarbon reactant comprises ≥90.0 wt. % of the methane, based on the weight of the hydrocarbon reactant.

7. The process of claim 1, wherein (i) the oxidant comprises molecular oxygen obtained from air; (ii) the hydrocarbon reactant comprises ≥99.0 wt. % of the methane, based on the weight of the hydrocarbon reactant; and (iii) the catalytic conversion of step (c) (ii) is carried out at a methane:molecular oxygen molar ratio in the range of 10.0 to 20.0.

8. The process of claim 1, wherein, between the first time interval and the second time interval, a sweep fluid is passed through the reverse-flow reactor to remove at least a portion the combustion gas.

9. The process of claim 1, wherein the first hydrocarbon conversion catalyst is configured in an upstream location of the reverse-flow reactor and the second hydrocarbon conversion catalyst is configured in a downstream location of the reverse-flow reactor, with the reverse-flow reactor being further configured for passing the heating fluid from the upstream location toward the downstream location.

10. The process of claim 1, wherein the first hydrocarbon conversion catalyst and the oxygen storage material are included as dispersed particles in pores of the second hydrocarbon conversion catalyst.

11. The process of claim 1, wherein:
the thermal mass comprises a first thermal mass segment and a second thermal mass segment; and
during the second time interval, the first thermal mass segment is heated and the second thermal segment mass is cooled.

12. The process of claim 11, wherein the reverse-flow reactor is an adiabatic reverse-flow reactor.

13. The process of claim 12, wherein (i)≥50.0 wt. % of the first thermal mass segment, based on total weight of the first thermal mass segment, is located in a first region of the reverse-flow reactor, (ii)≥50.0 wt. % of the second thermal mass segment, based on total weight of the second thermal mass segment, is located in a second region of the reverse-flow reactor, and (iii)≥50.0 wt. % of 1) the first hydrocarbon conversion catalyst and 2) the oxygen storage material are deposited on or in the thermal mass, based on total respective weights of each of the catalysts and oxygen storage material, are located on or in the first thermal mass segment of the first region.

14. The process of claim 13, wherein the process further comprises the steps of:
(b1) during the first time interval,
  i. passing the heating fluid's oxidant from the first thermal mass segment to the second thermal mass segment to heat the first thermal mass segment and the second thermal mass segment,
  ii. the storing of step (b)(ii) is carried out by storing at least the second portion of the oxidant with the oxygen storage material as the oxidant is passed from the first thermal mass segment to the second thermal mass segment, and
  iii. lessening or discontinuing the passing of the heating fluid's oxidant from the first thermal mass segment to the second thermal mass segment.

* * * * *